(12) United States Patent
Peterson

(10) Patent No.: US 8,637,468 B2
(45) Date of Patent: Jan. 28, 2014

(54) SYNTHETIC CHOLESTERYLAMINE-LINKER DERIVATIVES FOR AGENT DELIVERY INTO CELLS

(75) Inventor: Blake R. Peterson, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 0 days.

(21) Appl. No.: 13/390,327

(22) PCT Filed: Aug. 12, 2010

(86) PCT No.: PCT/US2010/045358
§ 371 (c)(1),
(2), (4) Date: May 2, 2012

(87) PCT Pub. No.: WO2011/019942
PCT Pub. Date: Feb. 17, 2011

(65) Prior Publication Data
US 2012/0208771 A1     Aug. 16, 2012

Related U.S. Application Data

(60) Provisional application No. 61/233,363, filed on Aug. 12, 2009.

(51) Int. Cl.
*A61K 38/00* (2006.01)
*A61K 47/00* (2006.01)

(52) U.S. Cl.
USPC .......................................... 514/20.9; 514/1.2

(58) Field of Classification Search
None
See application file for complete search history.

(56) References Cited

U.S. PATENT DOCUMENTS

| 4,560,512 A | 12/1985 | Firestone |
| 5,041,291 A | 8/1991 | Bader |
| 5,283,185 A | 2/1994 | Epand |
| 5,948,925 A | 9/1999 | Keynes |

OTHER PUBLICATIONS

Sun et al. Selective Disruption of Early/Recycling Endosomes: Release of Disulfide-Linked Cargo Mediated by a N-Alkyl-3β-Cholesterylamine-Capped Peptide. J Am Chem Soc. Aug. 6, 2008; 130(31): 10064-10065. The supplementary information is also attached in the article.*

Boonyarattanakalin et al. Endocytic Delivery of Vancomycin Mediated by a Synthetic Cell Surface Receptor: Rescue of Bacterially Infected Mammalian Cells and Tissue Targeting in Vivo. J. Am. Chem. Soc. 2007, 129, 268-269.*

Blagbrough, I.S. et al., "Polyamines and novel polyamine conjugates interact with DNA in ways that can be exploited in non-viral gene therapy", Biochemical Society Transactions, 2003, vol. 31, pp. 397-406.

Mignet, N. et al., Anionic pH-sensitive pegylated lipoplexes to deliver DNA to tumors, International Journal of Pharmaceutics, 2008, vol. 361, pp. 194-201.

* cited by examiner

*Primary Examiner* — Karlheinz R Skowronek
*Assistant Examiner* — Jia-Hai Lee
(74) *Attorney, Agent, or Firm* — Maschoff Brennan, PLLC

(57) ABSTRACT

Synthetic cholesterylamine-linkers can include derivatives of cholesterol, cholesteryl, or sitosteryl coupled through the linker to an agent for delivery into cells. The cholesterylamines are thought to mimic cholesterol in the capacity and mechanism for enhanced entry into cells. The configuration of the cholesterylamine-linker that is thought to provide for enhanced entry into cells includes a cholesterylamine that is coupled to a linker from the amine, and which linker includes a negative charge at a spatial distance from the amine of the cholesterylamine.

19 Claims, 15 Drawing Sheets

Doxorubicin

Dox-1

Dox-2

Dox-3

SYNTHETIC CHOLESTERYLAMINE-LINKER DERIVATIVES FOR AGENT DELIVERY INTO CELLS

CROSS-REFERENCE TO RELATED APPLICATIONS

This application is a U.S. Nationalization of PCT Application Number PCT/US2010/045358, filed on Aug. 12, 2010,

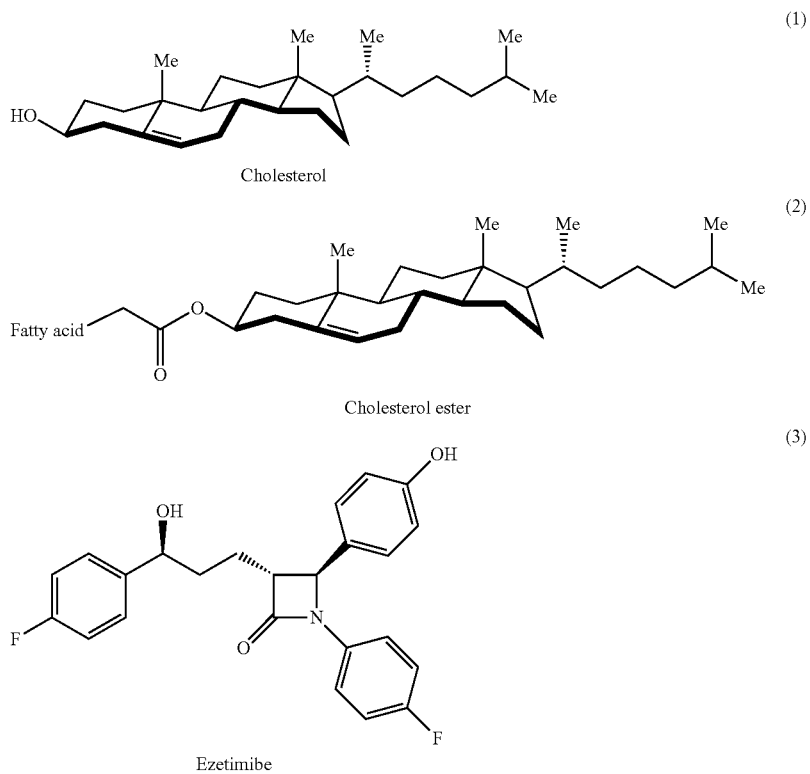

which claims benefit of U.S. provisional application 61/233,363, filed on Aug. 12, 2009, the entireties of which are incorporated herein by reference.

This invention was made with government support under R01-CA83831 awarded by the National Institutes of Health. The government has certain rights in the invention.

BACKGROUND OF THE INVENTION

Cholesterol (Compound 1) is a critical constituent of membranes of animal cells. Cells acquire exogenous forms of this sterol through multiple mechanisms involving structurally distinct cell surface receptors. Lipoprotein particles such as low-density lipoprotein (LDL) and high-density lipoprotein (HDL) carry cholesteryl esters (Compound 2) and associated protein and lipid components throughout the bloodstream. Cells expressing LDL and HDL receptors actively internalize these natural nanoparticles via receptor-mediated endocytosis. In contrast, cellular uptake of free (unesterified) cholesterol, found in mixed micelles, involves the direct binding of this sterol to other receptors, such as Niemann-Pick C1-like protein (NPC1L1) on cell surfaces. This receptor for free cholesterol was identified as a target of ezetimibe (Compound 3), a drug used to treat hypercholesterolemia. Recent studies suggest that although NPC1L1 is a primary target of ezetimibe and its glucuronide metabolite, other proteins such as the HDL receptor SR-BI can also be inhibited by this drug. Also, there may be other mechanisms for cholesterol, cholesteryl ester, ezetimibe, or other agent to enter into cells, and such mechanisms may be exploited for delivery of agents (e.g., diagnostic, therapeutic, imaging, or other) into cells.

Some previously identified derivatives of cholesterol have numerous important biological applications. These known compounds, particularly cholesteryl carbamates, have been used to facilitate the delivery of small inhibitory RNA (siRNA), enhance DNA transfection, probe cellular membrane subdomains, and have been proposed for tumor targeting applications. For example, cellular uptake of cholesteryl carbamate-conjugated siRNA in vitro and in vivo is similar to uptake of cholesteryl esters, requiring binding to HDL or LDL, followed by internalization via HDL or LDL receptors. This initial lipoprotein-binding step presumably slows uptake as compared to internalization of free cholesterol via direct binding to cell surface receptors. Because cholesteryl carbamate-linked siRNAs are only internalized after binding lipoproteins, the presence of high concentrations of serum in media typically used for cell culture (e.g. 10%) substantially reduces the activity of these compounds, likely because of competition between serum lipoproteins and cognate cell surface receptors.

Therefore, there is a need for continued development of cholesterol derivatives for increasing the binding of cells and efficacy of delivery of agents into cells.

BRIEF SUMMARY OF THE INVENTION

In one embodiment, a compound can be configured for delivery into cells. The compound can include a structure of Formula 1 or Formula 2 or derivative, salt, or prodrug thereof. Preferably, the compound can include a structure of Formula 3 or Formula 4 or derivative, salt, or prodrug thereof. More preferably, the compound can include a structure of Formula 5 or Formula 6 or derivative, salt, or prodrug thereof.

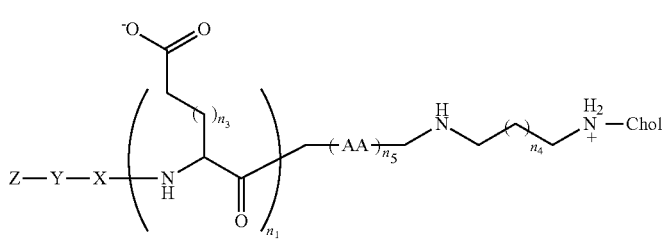

Formula 1

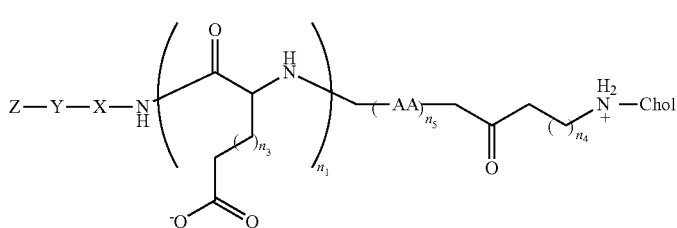

Formula 2

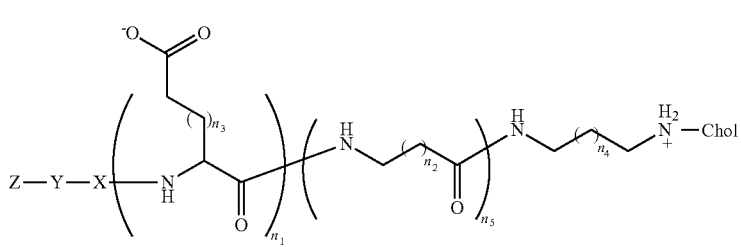

Formula 3

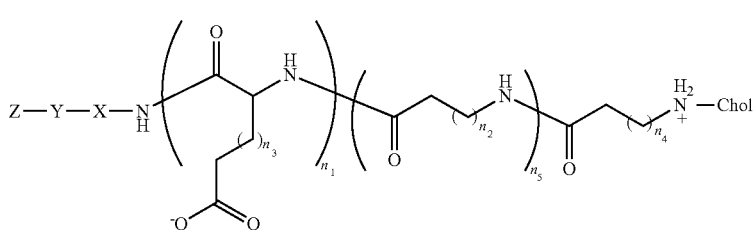

Formula 4

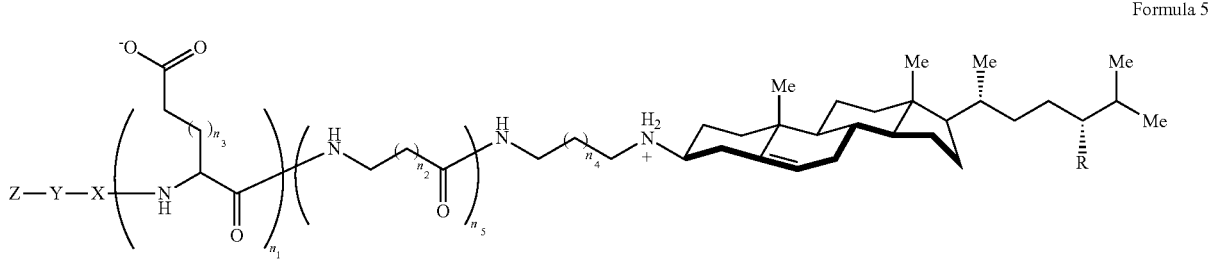

Formula 5

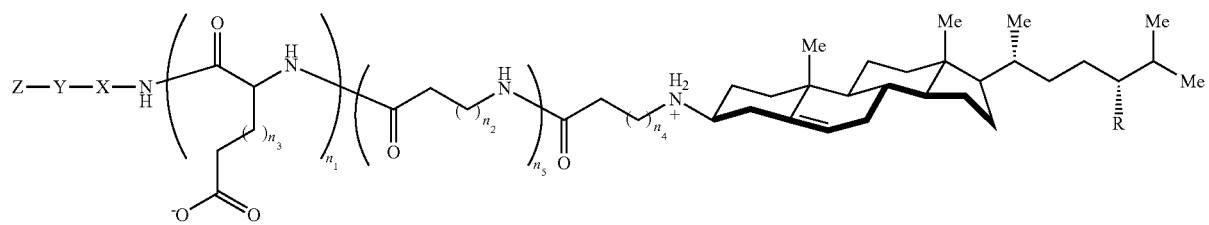

Formula 6

In Formulae 1-6: $n_1$ is 1-6; $n_2$ is 0-6; $n_3$ is 0-6; $n_4$ is 0-6; n5 is 1-10; AA can be one or more natural or non-natural amino acids, essential amino acids, or non-essential amino acids, or derivatives of amino acids having L or D configuration; Chol is a cholesterol derivative; R is hydrogen, methyl, ethyl, alkyl, or the like; X is nothing or a coupling group; Y is nothing or a linker; and Z is an agent for delivery into a cell. The residue within the bracket $n_1$ can be glutamic acid or aspartic acid, and can have L or D configuration.

In one embodiment, the cholesterol derivative is selected from the group consisting of cholesterol, dihydrocholesterol, sitosterol, cholesteryl, dihydrocholesteryl, or derivative thereof. In one aspect, the cholesterol derivative is a cholesteryl, dihydrocholesteryl, or sitosterol so that the compound includes a cholesterylamine, dihydrocholesterylamine, or sitosterylamine.

In one embodiment, the linker Y is selected from a straight chain or branched or cyclic substituted or unsubstituted alkyl group having C1-C100, a polypeptide, a polynucleotide, polysaccharide, a polyethylene glycol, a biodegradable linker, or combinations thereof.

In one embodiment, the coupling group X includes an amide, ether, ester, carbamate, alkyl, aryl, alkene, triazole, amine, or alkanol. Alternatively, the coupling group X can be derived from a coupling reaction between the linker and a coupling agent selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, derivatives thereof, and combinations thereof.

In one embodiment, the agent Z is selected from therapeutic agents, imaging agents, diagnostic agents, assay agents, toxic agents, or combinations thereof. Example of the agent Z include a protein, peptide, polypeptide, nucleic acid, RNA, DNA, RNA/DNA hybrid, PNA, morpholinos, oligomers, siRNA, carbohydrates, lipids, markers, luminophores, tracer substances, molecular probes, oligopeptides, drugs, prodrug, a small molecule, or combinations thereof.

In one embodiment, the compound includes one or more beta-alanine residues between the X and the Chol.

In one embodiment, the compound includes wherein the compound has a structure of Formula 7 or derivative, salt, or prodrug thereof.

Formula 7

In one embodiment, the compounds can be prepared into pharmaceutical compositions. Such a pharmaceutical composition can include a pharmaceutically acceptable carrier having the compound. The composition can alternatively be a diagnostic composition, assay composition, imaging composition, or other composition that has a use.

In one embodiment, a method of delivering an agent into a cell can include: providing a compound as described herein having an agent; and administering the compound to the cell. The administering can be in vivo, or it can be in vitro. When the agent is a therapeutic agent, the cell can be in a subject in need of the agent. Also, the agent can be a therapeutic agent for treating and/or inhibiting a disease or symptom of the disease, and the therapeutic agent can be administered in a therapeutically effective amount to treat and/or inhibit the disease or symptom of the disease.

In one embodiment, a system for delivering an agent into a cell can include: a compound as described herein; and a release compound configured for releasing the compound into cytoplasm of the cell. In one option, the release compound can include an endosomal disrupting agent.

In one embodiment, a cell can include a compound as described herein such as the compounds of Formulas 1-5 or other compounds of the invention.

It has been found that cells acquire exogenous cholesterol, a constituent of animal cell membranes, through multiple mechanisms involving structurally distinct cell surface receptors. Whereas cholesteryl esters are incorporated into lipoprotein particles that bind LDL and HDL receptors, free (unesterifed) cholesterol can bind directly to cell surface receptors, such as Niemann-Pick C1-like protein (NPC1L1). These principles were used to design novel mimics of free cholesterol. Saturation binding assays were used to compare the cellular binding profiles of fluorescent N-alkyl-3β-cholesterylamines, a N-alkyl-3β-sitosterylamine, a N-acyl-3β-cholesterylamine, a cholesteryl ether, a cholesteryl ester, and a cholesteryl carbamate bearing one or more glutamic acids between the fluorophore and the membrane anchor. In contrast to the other membrane anchors, N-alkyl-3β-cholesterylamines linked through β-alanine and glutamic acid residue(s) to the Pennsylvania Green ("PG") fluorophore were found to surprisingly and unexpectedly mimic free cholesterol, and to bind mammalian cell surfaces with high efficacy and submicromolar affinity in the presence of 10% serum. This binding was predominantly receptor-mediated as evidenced by >50% inhibition upon coaddition with either excess ezetimibe or free cholesterol. The compounds herein have been identified in view of this information, and are useful as probes of membrane biology and can be useful tools for the delivery of impermeable molecules into cells both in vitro and in vivo.

These and other embodiments and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Figure 1:
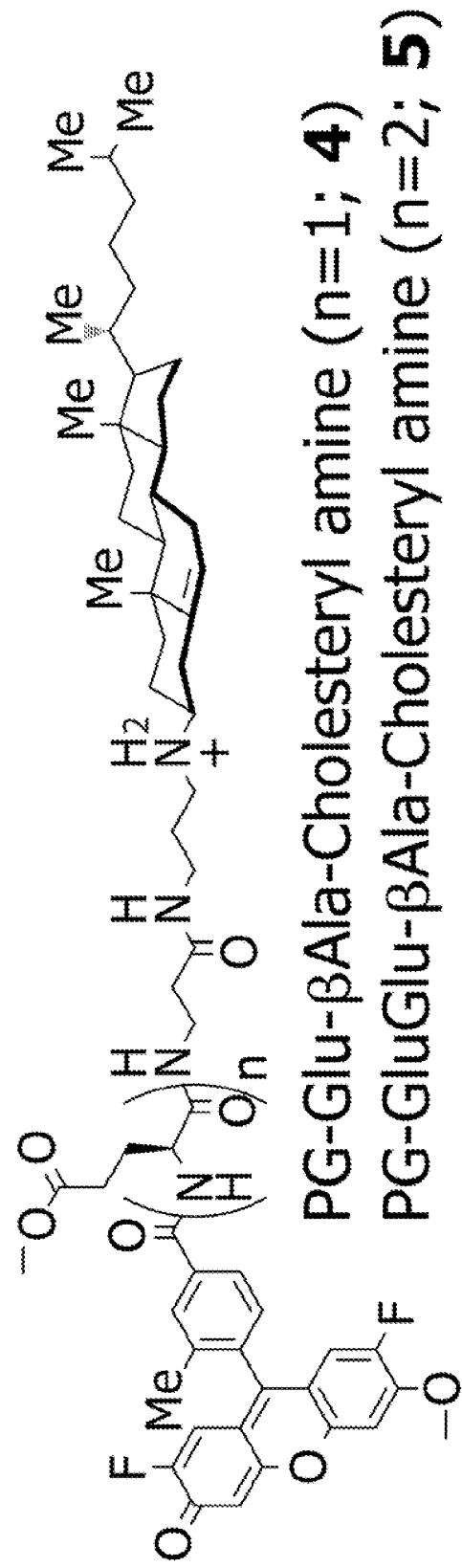
FIG. 1 illustrates the chemical structures of embodiments of cholesterylamine-linkers linked to PennGreen (PG, which is a luminophore), where the linkers have one (compound 4) or more (compound 5) negative charges at a spatial distance from the cholesteryl amine.
Figure 2:
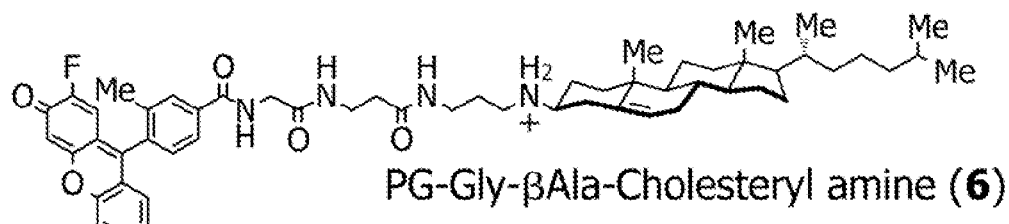
FIG. 2 illustrates chemical structures of embodiments of controls that lack the linker having the one or more negative charges at a spatial distance from the cholesterylamine (compounds 6-7), do not include a cholesteryl (e.g., sitosterylamine, compound 8) or do not include cholesterylamines (e.g., cholesteryl ether (compound 9), cholesteryl amide (compound 10), cholesteryl ester (compound 11), cholesteryl carbamate (compound 12).
Figure 2:
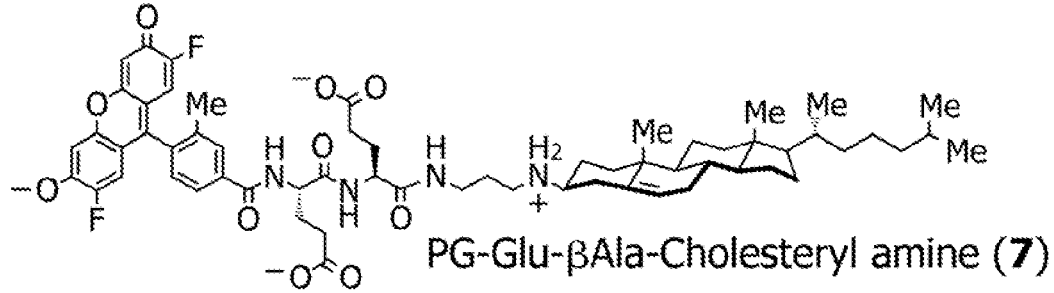
Figure 2:
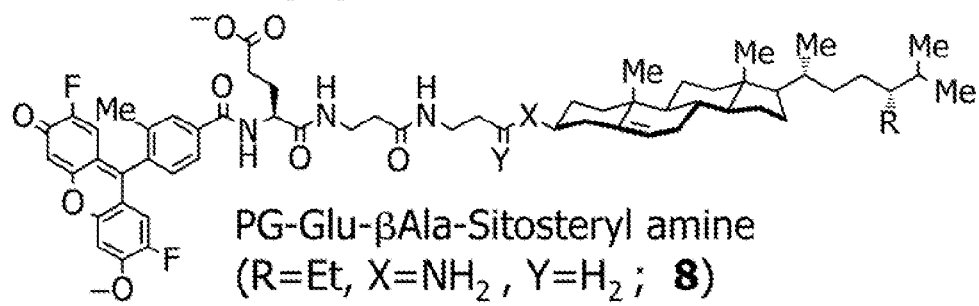
Figure 2:
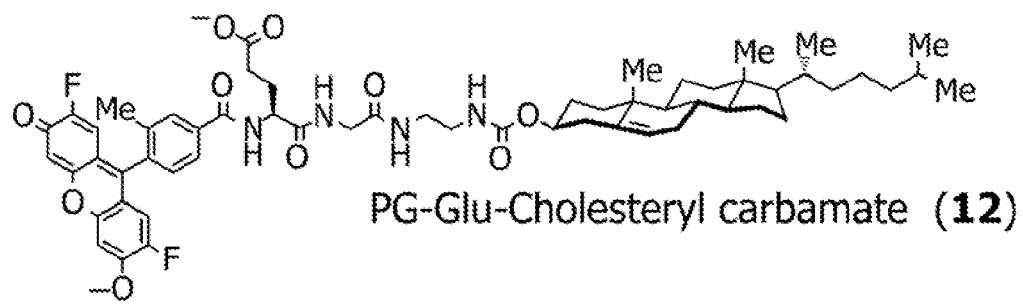

Generally, the present invention includes synthetic cholesterylamine-linkers and that can include derivatives of cholesterol or cholesteryl that can be coupled through the linker to an agent for delivery into cells. For convenience, the compounds described herein are generally referred to as "cholesterylamine-linkers," and may include a derivative of cholesterol or cholesteryl coupled to a linker that has an acid group that is spatially positioned from the cholesterylamine. The cholesterylamines are thought to mimic cholesterol in the capacity and mechanism for enhanced entry into cells. The configuration of the cholesterylamine-linker that is thought to provide for enhanced entry into cells includes a cholesterylamine that is coupled to a linker from the amine, and which linker includes a negative charge at a spatial distance from the amine of the cholesterylamine. The negative charge at a spatial distance from the cholesterylamine can facilitate entry of the cell without having to first bind to LDL or HDL and then entering into the cell. It is thought, without being bound thereto that the cholesterylamine-linkers described herein may interact differentially with serum proteins do to the negative charge, nevertheless, the data shows that the cholesterylamine-linkers described herein have superior binding and efficacy compared to cholesterylamine delivery platforms that do not include the negative charge at a spatial distance from the cholesteryl amine.

It is also thought that the cholesterylamine-linkers described herein may be useful for delivering an agent into a cell by the cholesterylamine-linker being a "ligand" having specificity for interacting and/or agonizing a Niemann-Pick C1-like Protein (NCP1L1) receptor so as to cause endocytosis of the ligand when bound to the receptor. Such endocytosis of the ligand results in the agent coupled thereto also being endocytosed into the cell. Substantially any agent can be linked to the ligand for delivery into the cell. However, now it has been found that some other mechanism for entry into the cell may be possible, nevertheless the ligand has superior delivery characteristics no matter the actual cellular mechanism for entry into the cell. The "ligands" described herein include N-alkyl derivatives of a 3β-cholesterylamine that have a linker linked to the agent, where the linker includes one or more negative charges at a spatial distance from the cholesterylamine. In one option, the linker can be configured to be a cleavable linker so that the agent can be released from the ligand, such as disulfides, hydrazones, imines, acetals, orthoesters, or other acid-labile or redox sensitive groups that allow release of agents in cells or tissues or others. Particular cells for delivery of the agent can include cells located on the intestinal wall of a subject.

The cholesterylamines have been prepared to mimic the cellular recognition properties of free cholesterol, where the protonated secondary amino group of N-alkyl-3β-cholesterylamines, as found in compounds 4-7, may function as a bioisostere for the 3β-hydroxyl group of cholesterol. In contradistinction to cholesteryl esters, cholesteryl carbamates, cholesteryl amides, or cholesteryl ethers, and structurally related compounds, which require lipoprotein-mediated cellular uptake, the cholesterylamine-linkers can bind directly to free cholesterol receptors, such as NPC1L1 on cell surfaces. Accordingly, the association rate and overall efficacy of delivery into cells is superior in relation. Also, it has been found that the addition of one or more anionic amino acids, such as glutamic acid, might affect binding to serum proteins and increase the affinity of these compounds for cells.

To investigate the structural determinants of recognition of cell surfaces by cholesterol derivatives and related compounds, we synthesized the fluorescent molecular probes shown as compounds 4-12. These probes were designed to systematically compare membrane anchors derived from N-alkyl-3β-cholesterylamine (compounds 4-7), a sitosteryl analogue (compound 8), a N-acyl-3β-cholesterylamine (compound 9), or cholesterol (compounds 9-12) linked to the Pennsylvania Green ("PG") fluorophore through amino acid subunits. The carbonyl linked to the steroid in amide 10, ester 11 or carbamate 12 is thought to be similar to natural cholesteryl esters, and this structural modification would correspondingly affect their ability to bind cell surfaces. The findings showed that compounds 4-5 were superior in entering cells. As such, the cholesterylamine-linkers described herein were prepared based on these two compounds, where the luminophore PG is substituted with an agent for delivery into a cell.

In view of compounds 4-5, the compounds of the invention can include a structure of Formula 1, Formula 2, Formula 3, Formula 4, Formula 5, or Formula 6 or derivative, salt, or prodrug thereof.

Formula 1

Formula 2

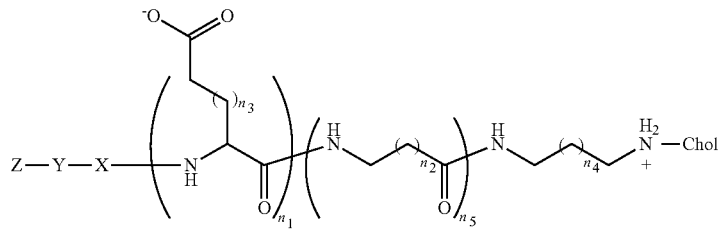

Formula 3

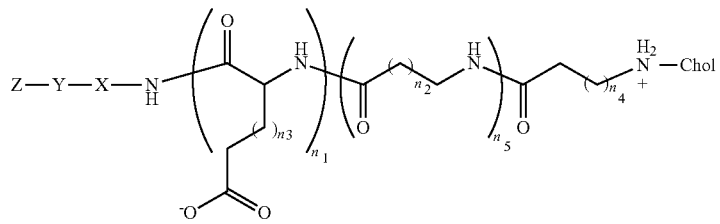

Formula 4

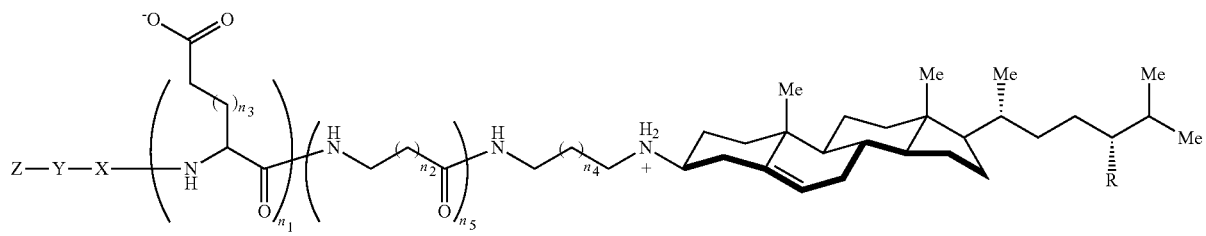

Formula 5

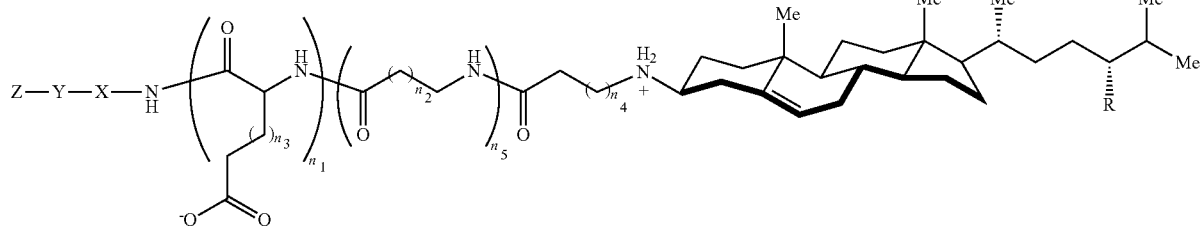

Formula 6

In Formulae 1-6: $n1$ is 1-6; $n2$ is 0-6; $n3$ is 0-6; $n4$ is 0-6; $n5$ is 1-10; AA can be one or more natural or non-natural amino acids, essential amino acids, or non-essential amino acids, or derivatives of amino acids having L or D configuration; Chol is a cholesterol derivative; R is hydrogen, methyl, ethyl, alkyl, or the like; X is nothing or a coupling group; Y is nothing or a linker; and Z is an agent for delivery into a cell. The residue within the bracket $n1$ can be glutamic acid or aspartic acid, and can have L or D configuration. An example of AA includes beta-alanine.

In one embodiment, $n1$ is 1; $n2$ is 1; $n3$ is 1; $n4$ is 1; $n5$ is 1-2.

In one embodiment, the cholesterol derivative is selected from the group consisting of cholesterol, dihydrocholesterol, sitosterol, cholesteryl, dihydrocholesteryl, or derivative thereof. In one aspect, the cholesterol derivative is a cholesteryl or dihydrocholesteryl or sitosteryl so that the compound includes a cholesterylamine or a dihydrocholesterylamine or a sitosterylamine. The Chol can be membrane anchor cholesterylamines (e.g., N-alkyl-3β-cholesterylamine, dihydrocholesterylamine, 3beta-amino-5 alpha-cholestane).

In one embodiment, the Chol of the formulas include a secondary amine, described by cholesterylamines. The ligands can be selected from derivatives of 3β-cholesterylamine or dihydrocholesterylamine or sitosterylamine. Examples of specific derivatives of 3β-cholesterylamines include N-alkyls that can be straight chain, branched, substituted or unsubstituted, from C1-C20, C2-C12, C1-C10, or the like. The ligand can also be 3β-amino-5alpha-cholestane, which is considered to be a derivative thereof.

The portion of the compound between X and Chol as shown in Formulae 1-4 is considered to be the primary linker region. Y is considered to be the secondary linker region, and the secondary linker Y is optional, and thereby the coupling group X is optional.

It has been found, for example, that the makeup of the linker region affects the partitioning of these compounds between the plasma membrane and endosomal compartments. As such, the primary linker includes at least one anionic moiety, and more preferably two or more separate or contiguous anionic moieties. Preferably, the anionic moiety is an amino acid having an acid side chain. Also preferably, the amino acid anionic moiety can be located adjacent or relatively close to (within 2-6 atoms) a beta-alanine. The anionic moieties can be any of a variety of components that present an anionic feature at physiological conditions within the blood of extracellular fluids. The anionic moieties on the linker have been found to enhance the ability of the cholesterylamine derivatives to bind or have affinity for the cells. The inclusion of one or more anionic moieties in the linker has surprising and unexpected results in that the cholesterylamines have enhanced ability to function as a ligand and promote endocytosis into early/recycling endosomes, especially when adjacent or associated with a beta-alanine in the primary linker. In part, this is surprising due to the fact that the cell membranes are overwhelming negative in charge by being comprised of anionic lipids, and one would expect that anionic linkers would be repulsed by the anionic cell membrane. While glutamic acid is shown in the primary linker, it may be substituted with aspartic acid.

In one embodiment, the linker Y is selected from a straight chain or branched or cyclic substituted or unsubstituted alkyl group having C1-C100, an aryl linker, a polypeptide, a polynucleotide, polysaccharide, a polyethylene glycol, a biodegradable linker, or combinations thereof. For example, the Y linker can be an alkyl chain that is a straight chain, branched, substituted or unsubstituted, from C1-C20, C2-C12, C1-C10, or the like. The linker can include amino acids and/or alkyl groups as described herein.

In one embodiment, the coupling group X includes an amide, ether, ester, carbamate, alkyl, aryl, alkene, triazole, amine, or alkanol. Alternatively, the coupling group X can be derived from a coupling reaction between the linker and a coupling agent selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, derivatives thereof, and combinations thereof.

In one embodiment, the agent Z is selected from therapeutic agents, imaging agents, diagnostic agents, toxic agents, or combinations thereof. Example of the agent Z include a protein, peptide, polypeptide, nucleic acid, RNA, DNA, RNA/DNA hybrid, PNA, morpholinos, oligomers, siRNA, carbohydrates, lipids, markers, luminophores, tracer substances, molecular probes, oligopeptides, drugs, prodrug, a small molecule, or combinations thereof.

In one embodiment, the agent can be an siRNA such that the compound can effect gene silencing in cells. The siRNA can be unmodified or modified with a 2' modification. Also, the siRNA can be modified by having an internucleotide linkage. The siRNA can be linked to the linker through the sense or antisense strand.

In one embodiment, the compound includes one or more beta-alanine residues between the X and the Chol.

In one embodiment, the compound includes wherein the compound has a structure of Formula 7 or derivative, salt, or prodrug thereof. Also, the negative moiety, shown as glutamic acid, can be repeated one or more times consecutively.

Formula 7

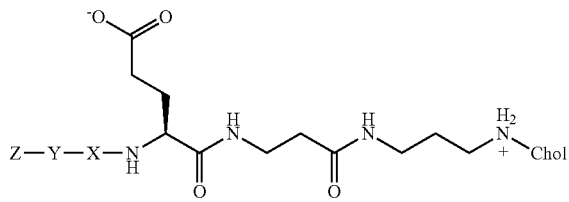

The agent can also be a reporter molecule. The reporter molecule may be, but is not limited to, a visible dye, fluorescent dye, an isotope label, a radioactive tag, a molecular label, a drug label, a cleavable label, or a hydrolyzable label. Non-limiting examples of visible or fluorescent dye reporter molecules may include fluorescein isothiocyanate (FITC), fluorescein, rhodamine, coumarin, and cyanine as well as others. Non-limiting examples of isotope labels may include 18O, 15N, 13C, or 2H, 3H. Non-limiting radioactive tags may include 18F or 14C. Non-limiting examples of drug labels may include acetyl salicylic acid, nicotine, ciprosloxacin, quinolone, levosloxacin, provasloxacin, citric acid, and acetaminophen.

Suitable examples of Y linkers and/or X coupling groups can be formed from or include a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, hydrazones, imines, acetals, orthoesters, or other acid-labile or redox sensitive groups that allow release of agents in cells or tissues, photopolymerizable moiety, acrylic acid grafted cellulose, hydroxymethyl methacrylate grafted cellulose, poly(vinyl alcohol) grafted cellulose, poly(vinyl amine) grafted cellulose, acrylamide grafted cellulose, polyallylamine-grafted cellulose, cellulose containing gluconic acid, derivatives thereof, and combinations thereof. Also, the Y linker or X coupling group can be prepared by "click" reactions which are known in the art, such as a 1,3 dipolar cycloaddition of an azide and alkyne or similar condensation to yield a triazole or other linking subunit.

Suitable examples of dithio diacids include, but are not limited to, dithio dicarboxylic acid, dithio dipropanoic acid, dithio dibutanoic acid, dithio dipentanoic acid, dithio dihexanoic acid, and derivatives and combinations thereof. Specific examples of dithio diacids can include 16-carboxyhexadecyl disulfide, 5,5' dithiobis(2-nitrobenzoic acid), 2,2'-dithiodibenzoic acid, 4,4'-dithiodibutyric acid, 3,3'-dithiodipropionic acid and 6,6'-dithiodinicotinic acid.

In one aspect, the linking is reversible. For example, the linking with the dithio or diacids listed above can be reversed with the addition of dithiothreitol (DTT) or a similar reducing reagent that can break the disulfide linkage in the linker. The cross-linking can be reinitiated by addition of an oxidizing agent such as, but not limited to, hydrogen peroxide.

In one aspect, suitable examples of dicarboxylic acids include, but are not limited to, oxalic acid, malonic acid, succinic acid, glutaric acid, adipic acid, pimelic acid, suberic acid, azelaic acid, sebacic acid, phthalic acid, maleic acid, isophthalic acid, terephthalic acid, and derivatives and combinations thereof.

In one embodiment, the linker can include an acrylic moiety such as but not limited to acrylic acid, methacrylic acid, hydroxyethyl methacrylate, hydroxypropyl methacrylate, acrylamide, glucose methacrylate, galactose methacrylate, aminoethyl methacrylate, derivatives and combinations thereof.

In one embodiment, the linker includes styrene, 4-vinylbenzoic acid, 4-vinylbenzenesulfonic acid, vinyl pyridine, vinyl phenol, divinylbenzene, 4-cyanostyrene, or derivative or combination thereof.

In one embodiment, the linker includes a vinyl carboxylic acid, vinyl acetate, vinyl alcohol, vinyl amine, vinyl propionate, vinylbutyrate, vinylbutryaldehyde, or derivative or combination thereof.

In one embodiment, the linker includes a disulfide such as but not limited to 16-carboxyhexadecyl disulfide, 5,5' dithiobis(2-nitrobenzoic acid), 2,2'-dithiodibenzoic acid, 4,4'-dithiodibutyric acid, 6,6'-dithiodinicotinic acid, 3,3'-dithiodipropionic acid, derivatives thereof and combinations thereof.

In one embodiment, the coupling group X may be derived from a reaction with hydroxybenzotriazole (HOBt) and a carbodiimide reagent. Suitable examples of carbodiimide reagents include, but are not limited to, N,N'-dicyclohexyl-carbodiimide (DCC), N,N'-diisopropylcarbodiimide (DIC), 1-Ethyl-3-(3-dimethylaminopropyl)carbodiimide (EDC), and combinations thereof.

The Y linker may also include a peptidomimetric element such as a peptoid or other peptide-like structure.

In Formula 1-6, the carbons can be substituted with "R" groups. Also, the linker Y can be substituted with "R" groups or may be considered an "R" group. The R groups can be independently selected from substituents selected from the group of hydrogen, C1-C24 alkyl, C2-C24 alkenyl, C2-C24 alkynyl, C5-C20 aryl, C6-C24 alkaryl, C6-C24 aralkyl, halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH2), mono-(C1-C24 alkyl)-substituted carbamoyl (—(CO)—NH(C1-C24 alkyl)), di-(C1-C24 alkyl)-substituted carbamoyl (—(CO)—N(C1-C24 alkyl)2), mono-substituted arylcarbamoyl (—(CO)—NH-aryl), thiocarbamoyl (—(CS)—NH2), carbamido (—NH—(CO)—NH2), cyano(—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH 2), mono- and di-(C1-C24 alkyl)-substituted amino, mono- and di-(C5-C20 aryl)-substituted amino, C2-C24 alkylamido (—NH—(CO)-alkyl), C6-C20 arylamido (—NH—(CO)-aryl), imino (—CR=NH where R is hydrogen, C1-C24 alkyl, C5-C20 aryl, C6-C24 alkaryl, C6-C24 aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO 2), nitroso (—NO), sulfo (—SO 2-OH), sulfonato (—S2-O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO2-aryl), phosphono (—P(O)(OH)2), phosphonato (—P(O)(O—)2), phosphinato (—P(O)(O—)), phospho (—PO2), phosphino (—PH2), derivatives thereof, and combinations thereof.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, preferably 1 to about 12 carbon atoms. The term "lower alkyl" intends an alkyl group of 1 to 6 carbon atoms. Preferred substituents identified as "C 1-C 6 alkyl" or "lower alkyl" contains 1 to 3 carbon atoms, and particularly preferred such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 20 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

In one embodiment, the cholesterylamine-linker-agent can be located within a cell. In one example, the one or more cells can include an intestinal cell, an endothelium cell, or epithelium cell. Examples of cell types can further include prokaryotic cells, eukaryotic cells, bacteria, archaea, epidermal, epidermal keratinocyte, epidermal basal cell, keratinocytes, basal cell, medullary hair shaft cell, cortical hair shaft cell, cuticular hair shaft cell, cuticular hair root sheath cell, hair matrix cell, wet stratified barrier epithelial cells, gland cells, hormone secreting cells, metabolism cells, storage cells, barrier function cells, ciliated cells, extracellular matrix secretion cells, contractile cells, blood cells, immune system cells, nervous system cells, pigment cells, germ cells, nurse cells, interstitial cells, or others as well as combinations thereof. There are approximately 210 specific cell types found in the human body and there are many more diseased cell types. Suitable examples of specific cell types include, but are not limited to, at least one of an epithelial cell, a hormone secreting cell, an extracellular matrix secretion cell, a contractile cell, a blood cell, an immune cell, a nerve cell, a pigment cell, a germ cell, a nurse cell, an interstitial cell, a cancerous cell, or a pre-cancerous cell, diseased cells thereof, and combinations thereof.

The cholesterylamine-linker-agent can be administered to a subject, such as an animal like mammals, birds, or other classification, with humans, dogs, cats, farm animals, zoo animals or other animal being the subject.

The cholesterylamine-linker-agent can be located in a composition formulated for any route of administration, in particular for oral, rectal, transdermal, subcutaneous, intravenous, intramuscular or intranasal administration. The compositions may be formulated in any conventional form, for example, as tablets, capsules, caplets, solutions, suspensions, dispersions, syrups, sprays, gels, suppositories, patches and emulsions. The compound can be formulated with a pharmaceutically acceptable carrier.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject lonidamine analogue or derivative from one organ, or portion of the body, to another organ, or portion of the body. Each carrier must be "acceptable" in the sense of being compatible with the other ingredients of the formulation and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the present invention may be administered in free form or in pharmaceutically acceptable salt form. Such salts may be prepared in conventional manner and exhibit the same order of activity as the free compounds. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed.

As used herein, the term "pharmaceutically acceptable ester" refers to esters which hydrolyze in vivo and include, but are not limited to, those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein.

A "therapeutically effective amount" is an amount of a compound of the present invention or a combination of two or more such compounds, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient, a therapeutically effective amount can be determined by methods known to those of skill in the art.

Experimental

Chemical reagents were purchased from Apptec, Acros, Aldrich, Alfa Aesar, EMD Biosciences, or TCI America, and were used without further purification. Solvents were from Aldrich or Fisher Scientific. Ezetimibe (Zetia®), obtained from a local pharmacy, was isolated in pure form by extraction of crushed tablets with CH2Cl2/ddw, drying the organic layer over anhydrous Na2SO4, and removal of solvent in vacuo. Cell culture reagents were from Mediatech, BD Biosciences, Gibco, and Invitrogen. 3β-Amino-5-cholestene (compound 30), cholesteryloxypropan-1-amine (compound 27), 4-Carboxy-Pennsylvania Green NHS ester, compound 13, and compound 18 were synthesized. Anhydrous solvents were obtained after passage through a drying column of a solvent purification system from GlassContour/SG Waters (Nashua, N.H.). All reactions were performed under an atmosphere of dry argon or nitrogen. Reactions were monitored by analytical thin-layer chromatography on plates coated with 0.25 mm silica gel 60 F254 (EM Science). TLC plates were visualized by UV irradiation (254 nm) or stained with either phosphomolybdic acid (20%) in ethanol or ninhydrin in ethanol. Column chromatography employed Silica Gel (Dynamic Adsorbents, 40-63 μm). Preparative HPLC employed an Agilent 1200 Series preparative pump/gradient extension with a Hamilton PRP-1 (polystyrene-divinylbenzene) reverse-phase preparative column (10-25 μm particle size, 21.5 mm×25 cm) with a flow rate of 25.0 mL/min. Melting points were measured with a Thomas Hoover capillary melting point apparatus and are uncorrected. Infrared spectra were obtained with a Perkin Elmer Spectrum 100 FTIR. NMR spectra were obtained with a Bruker Avance-400 or DRX-500 instrument with chemical shifts reported in parts per million (ppm, δ) referenced to either CDCl3 (1H, 7.26 ppm; 13C, 77.16 ppm), CD3OD (1H, 3.34 ppm; 13C, 49.00 ppm), or (CD3)2S=O (1H, 2.50 ppm; 13C, 128.06 ppm). High-resolution mass spectra were obtained at the University of Kansas Mass Spectrometry Facility (ESI and EI). Peaks are reported as m/z.

Biological Assays and Protocols

Cell Culture

Jurkat lymphocytes (human acute leukemia, ATCC #TIB-152) were cultivated in Roswell Park Memorial Institute (RPMI) 1640 medium supplemented with Fetal Bovine Serum (FBS, 10%), penicillin (100 units/mL), and streptomycin (100 μg/mL) in a humidified 5% CO2 incubator at 37° C. Media used for cell culture and all wash steps contained antibiotics and 10% FBS unless otherwise noted.

Microscopy

An inverted Leica TCS SPE confocal laser-scanning microscope fitted with a Leica 63× oil-immersion objective was employed for imaging. Fluorescent probes were excited with a 488 nm solid-state laser and emitted photons were collected from 495-600 nm. Propidium iodide, used to counterstain dead cells red fluorescent, was excited with a 532 nm solid-state laser and emitted photons were collected from 650-800 nm. To image living cells, 50 μL of cells in media was pipetted to form a small droplet in the center of a coverslip fitted with a press-to-seal silicone isolator (Invitrogen). A microscope slide was added to the top of the coverslip to create a column of media containing living cells. To allow accurate comparisons of differences in cellular fluorescence, laser power and PMT gain settings were identical for all samples.

Saturation Binding Studies of Fluorescent Probes

Cells were suspended at 300,000 cells/mL in RPMI media containing 10% FBS. Ezetimibe (100 μM; diluted 1:1000 into media from a 100 mM stock in DMSO; 0.1% final DMSO concentration), free cholesterol (200 μM; diluted 1:10 into media from a 2 mM stock in DMSO; 10% final DMSO concentration to enhance cholesterol solubility) or vehicle control (DMSO) was added in competition experiments. Cell suspensions containing the competitor or vehicle control were prepared as 1 mL aliquots in 1.5 mL eppindorf tubes. Fluorescent probes were added at concentrations from 0 nM to 2500 nM (diluted 1:1000 into media from stocks in DMSO). Once the probe was added and well mixed, the samples were split into three tubes each containing 330 μL. Cells were incubated at 16° C. for 10 min or 37° C. for 5 minutes to limit endocytosis. After this incubation, the samples were washed once with RPMI 1640 containing 0.5% FBS (to minimize efflux of the probe from the cell surface) and propidium iodide (3 μM). Samples were immediately analyzed by flow cytometry or confocal laser-scanning microscopy.

Flow Cytometry

Populations of 10,000 Jurkat cells were analyzed for each sample using an Accuri C6 flow cytometer equipped with 488 nm and 640 nm solid-state lasers. Live cells were gated using both forward scattering (FSC) and side scattering (SSC) dot plots to identify cellular physical properties of size and granularity and propidium iodide to identify cells with compromised membranes. The average cellular fluorescence upon excitation at 488 nm was plotted against probe concentration, and the data analyzed as total binding (no competitor added) and a linear non-specific binding component (with cholesterol or ezetimibe as a specific competitor) to calculate specific binding curves. Using GraphPad Prism 5.0 software, these curves were analyzed with a one site with hill slope binding model to determine the relative apparent Kd and Bmax values listed in Table 1 below.

TABLE 1

| Compound | $K_{d, app}$ (nM, 16° C.) | $B_{max}$ (×10$^5$, 16° C.) | $K_{d, app}$ (nM, 37° C.) | $B_{max}$ (×10$^5$, 37° C.) |
|---|---|---|---|---|
| 4 | 403 ± 49 | 2.31 ± 0.14 | 344 ± 32 | 2.54 ± 0.12 |
| 5 | 767 ± 244 | 3.93 ± 0.64 | 449 ± 74 | 3.01 ± 0.26 |
| 6 | Ambig.[a] | Ambig.[a] | NC[b] | NC[b] |
| 7 | Ambig.[a] | Ambig.[a] | 1540 ± 1140 | 3.2 ± 1.3 |
| 8 | 286 ± 27 | 0.73 ± 0.03 | 435 ± 221 | 1.3 ± 0.29 |
| 9 | 954 ± 285 | 1.68 ± 0.26 | Ambig.[a] | Ambig.[a] |
| 10 | 786 ± 358 | 1.86 ± 0.39 | 639 ± 190 | 2.2 ± 0.30 |
| 11 | NC[b] | NC[b] | NC[b] | NC[b] |
| 12 | NC[b] | NC[b] | NC[b] | NC[b] |

Figure 3:
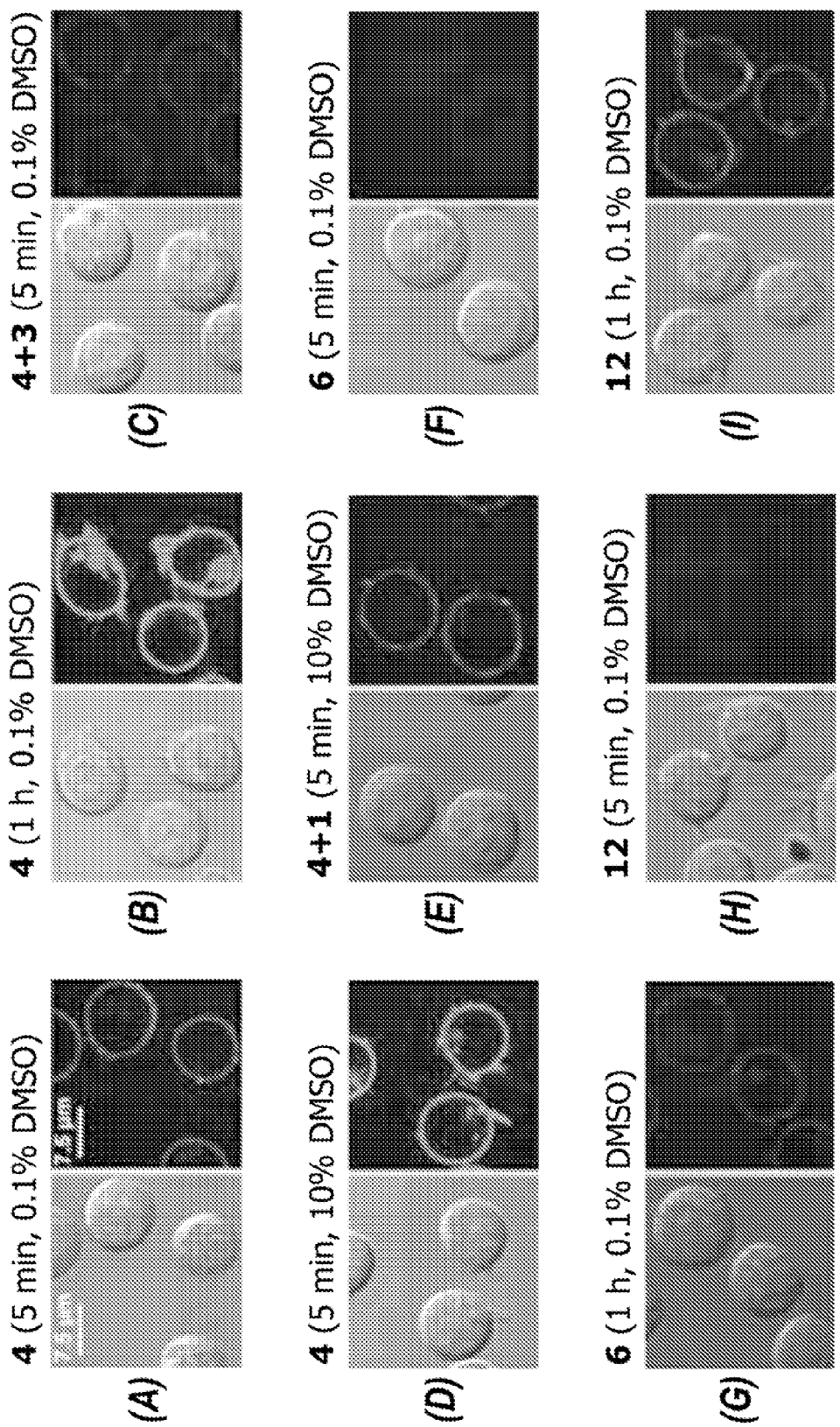
FIG. 3 includes micrographs showing differential interference contrast (DIC) and confocal laser scanning microscopy of living Jurkat lymphocytes in media containing 10% serum treated at 37° C. with fluorescent compound 4 (Panels A-E), compound 6 (F-G), and compound 12 (H-I) for 5 min or 1 h (2 µM). In C and D, ezetimibe (compound 3, 100 µM in 0.1% DMSO) and cholesterol (compound 1, 200 µM in 10% DMSO) were included as competitors to block uptake via cell surface receptors.

As shown in FIG. 3, confocal laser scanning microscopy was employed to compare living Jurkat lymphocytes after treatment with compounds 4, 6, and 12. These experiments demonstrated that cells treated with compound 4 (2 μM) for 5 minutes at 37° C. exhibit robust fluorescent staining of cellular plasma membranes. Cells examined after 1 hour showed enhanced cellular binding, uptake of the probe, and localization of compound 4 in transferrin-positive early/recycling endosomes (FIG. 3, panel B). Binding of compound 4 (and compound 5) to cell surfaces was predominantly receptor-mediated as evidenced by >50% inhibition upon coaddition with either excess ezetimibe (compound 3, 100 μM) or free cholesterol (compound 1, 200 μM), indicating that these compounds recognize cell surfaces as mimics of free cholesterol. Comparison of compound 4 with compound 6 lacking the glutamic acid residue in the linker region revealed that the anionic moiety of compound 4 may be important for rapid high affinity/efficacy binding to cells (FIG. 3, compare panels A and E). Moreover, despite the presence of a structurally analogous glutamic acid, the cholesteryl carbamate compound 12 showed substantially lower cellular binding and cellular uptake compared with compound 4. This shows that compound 12 is taken into a cell by a different pathway compared to compound 4.

Figure 4A:
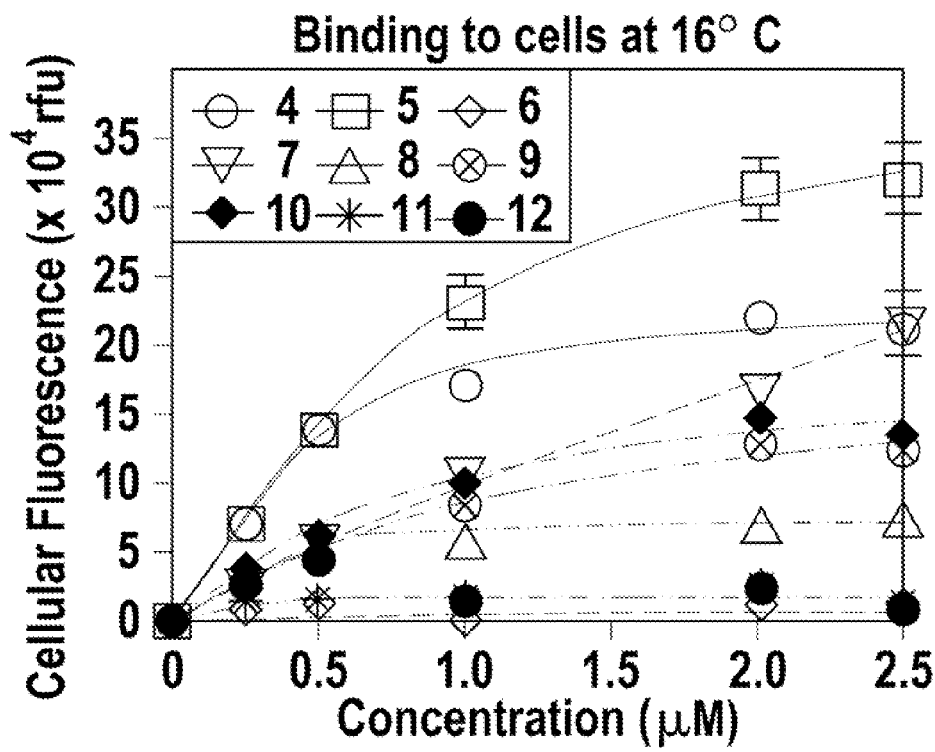
FIGS. 4A-4B include graphs that illustrate the specific binding curves calculated after association of compounds 4-12 with plasma membranes of living Jurkat lymphocytes in media containing 10% serum. Cells were treated with compounds 4-12 for 10 min (FIG. 4A) or 5 min (FIG. 4B) and analyzed by flow cytometry with and without free cholesterol (200 µM) in saturation binding experiments.
Figure 4B:
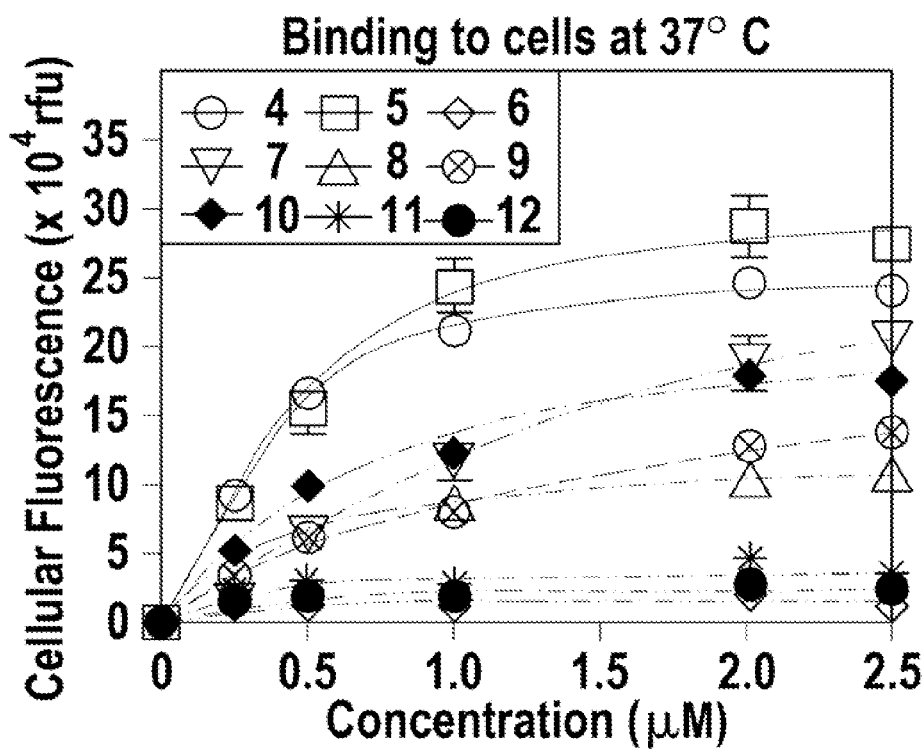
Figure 5:
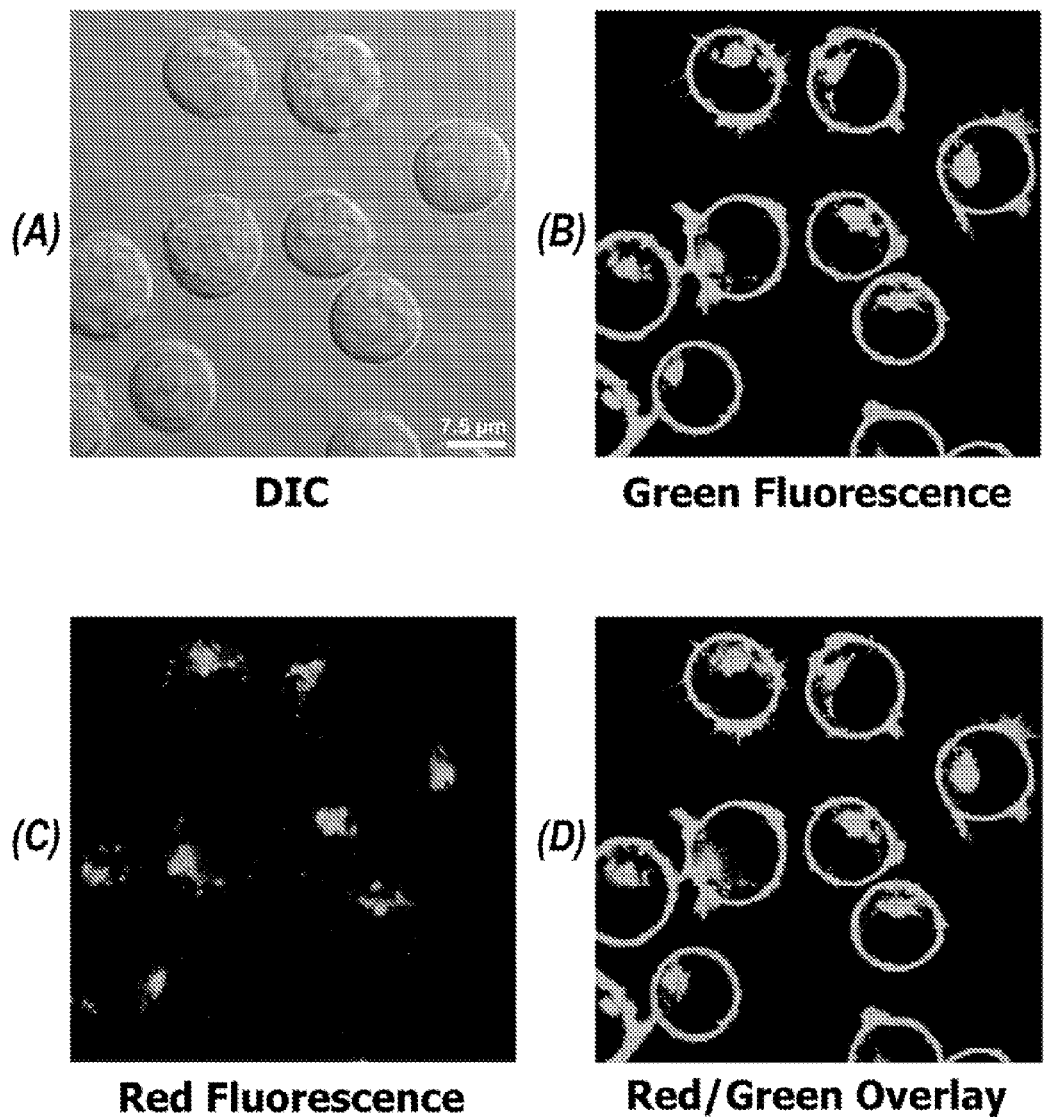
FIG. 5 includes confocal and DIC micrographs of Jurkat cells treated with compound 4 and transferrin, Alexa Fluor 633 conjugate. Cells were treated with green fluorescent compound 4 (2 µM) for 1 h followed by addition of the red fluorescent transferrin conjugate (1 µM) for 10 min. Cells were washed with media and imaged by differential interference contrast (DIC) and confocal laser scanning microscopy. Colocalization of red (Panel C; light shade in black and white image) and green fluorescence (Panel B; light shade in black and white image) in early/recycling endosomes, shown as yellow in the overlay image (aggregation of light in Panel D), can be observed.
Figure 6A:
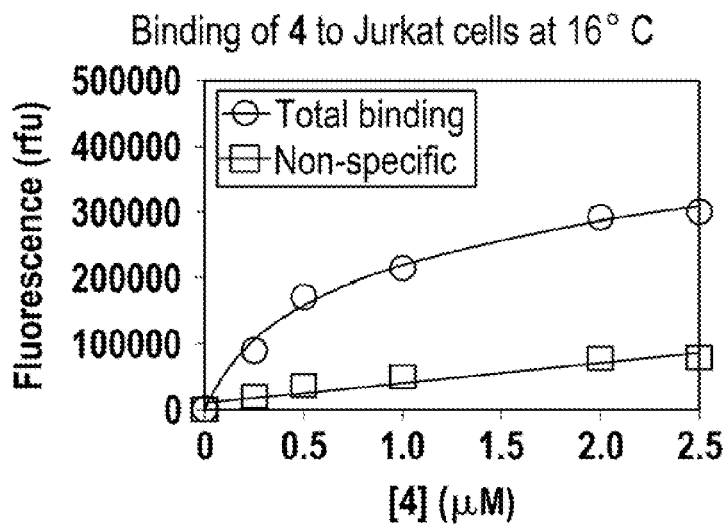
FIGS. 6A-6I include graphs that illustrate the total and non-specific binding of compounds 4-12 to Jurkat lymphocytes at 16° C. This data was used to calculate the specific binding curves shown in FIG. 4A. Compounds were added to cells for 10 min (10% DMSO) in the presence or absence of free cholesterol (200 µM). Cells were washed with fresh media (containing red fluorescent propidium iodide (3 µM) to counterstain dead cells) and the green fluorescence of compounds 4-12 bound to living cell surfaces was analyzed by flow cytometry.
Figure 6B:
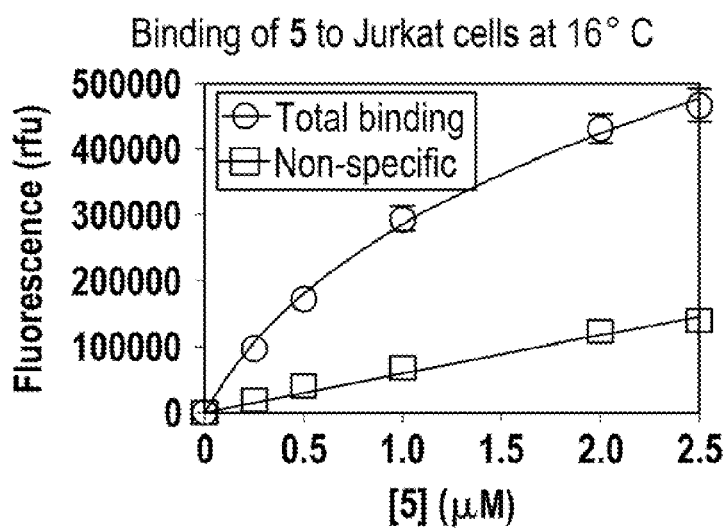
Figure 6C:
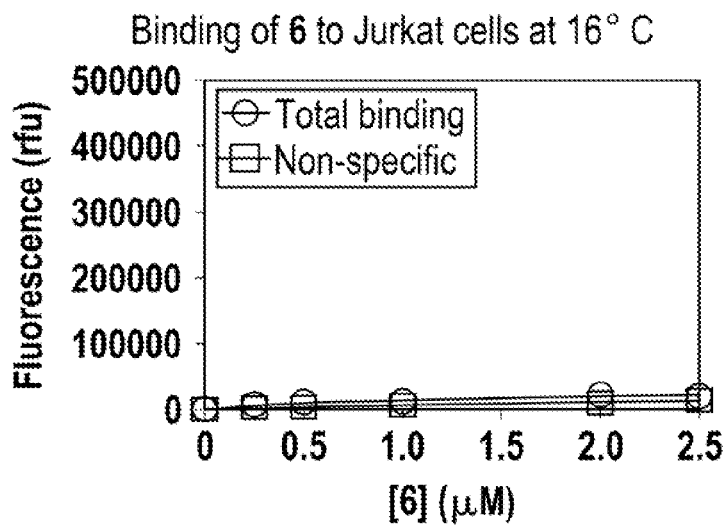
Figure 6D:
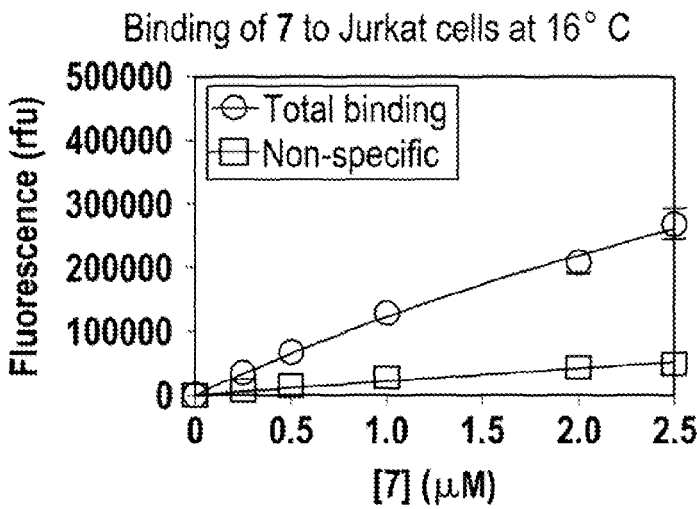
Figure 6E:
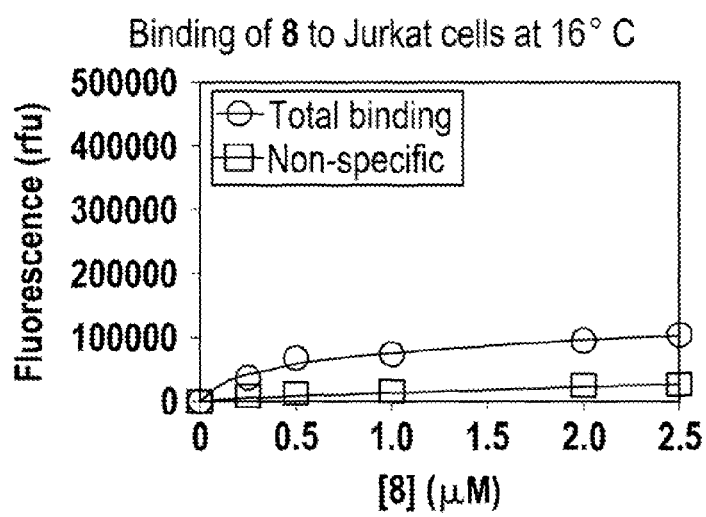
Figure 6F:
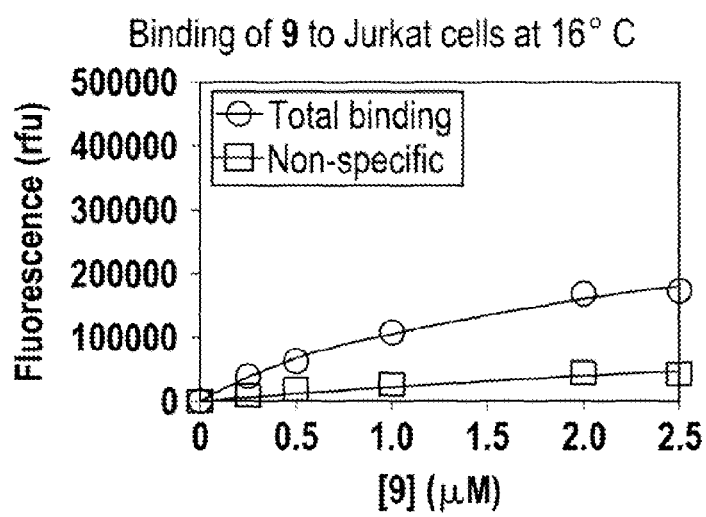
Figure 6G:
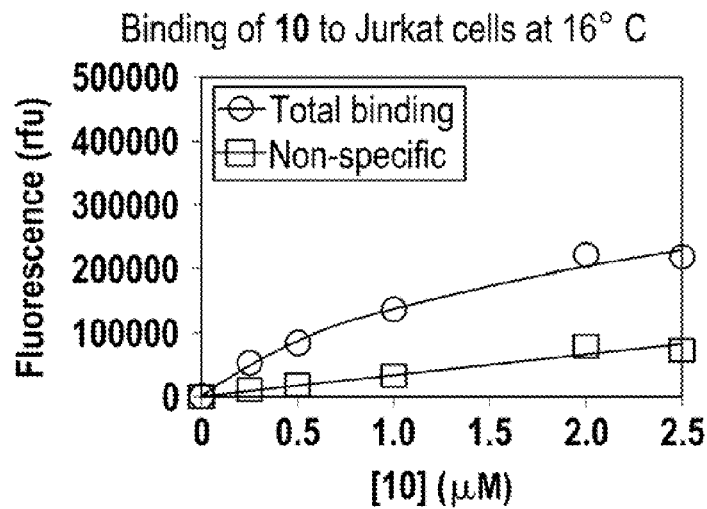
Figure 6H:
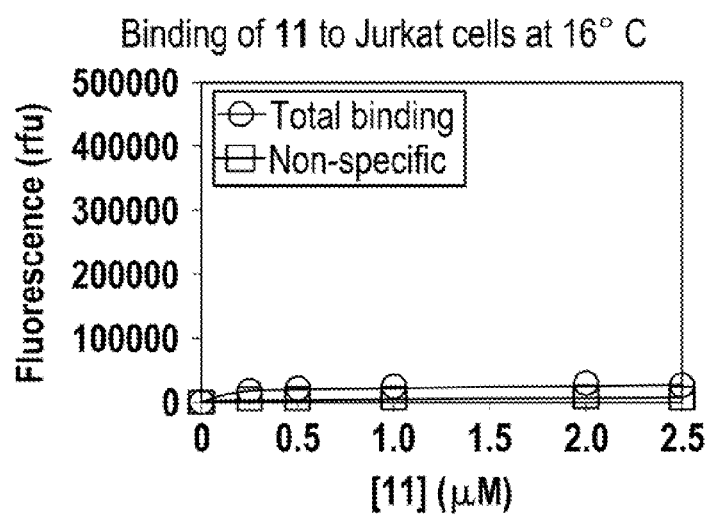
Figure 6I:
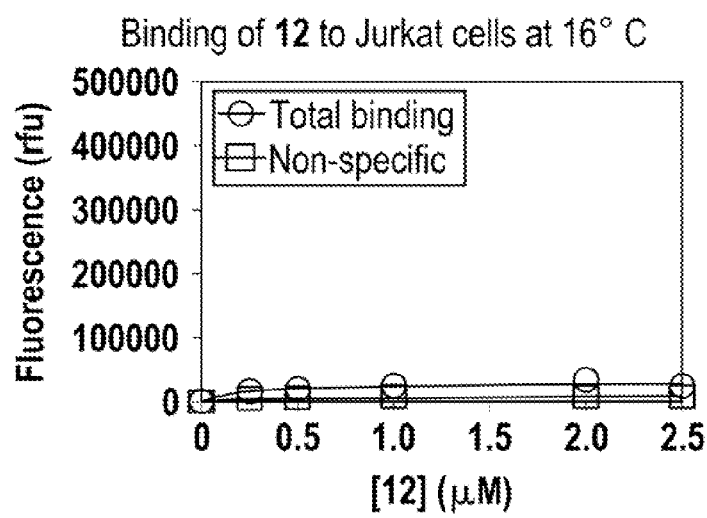
Figure 7A:
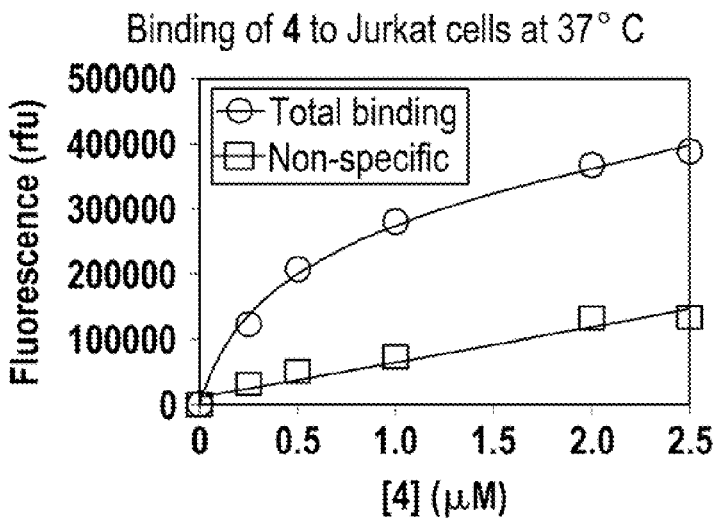
FIGS. 7A-7I include graphs that illustrate the total and non-specific binding of compounds 4-12 to Jurkat lymphocytes at 37° C. This data was used to calculate the specific binding curves shown in FIG. 4B. Compounds were added to cells for 5 min (10% DMSO) in the presence or absence of free cholesterol (200 µM). Cells were washed with fresh media (containing red fluorescent propidium iodide (3 µM) to counterstain dead cells) and the green fluorescence of compounds 4-12 bound to living cell surfaces was analyzed by flow cytometry.
Figure 7B:
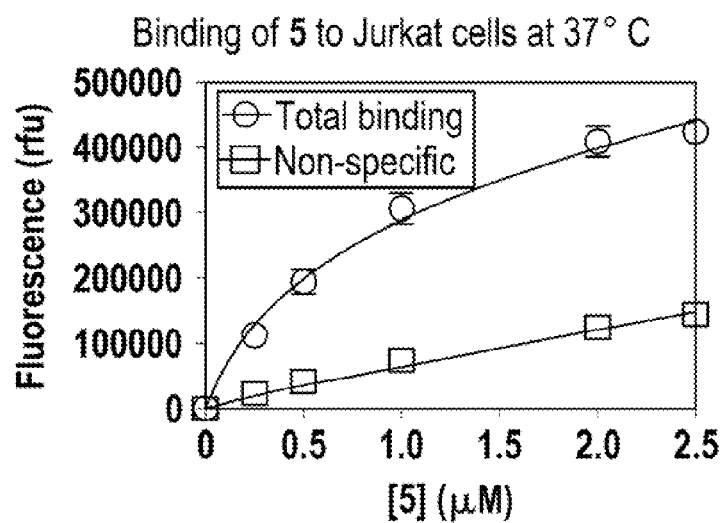
Figure 7C:
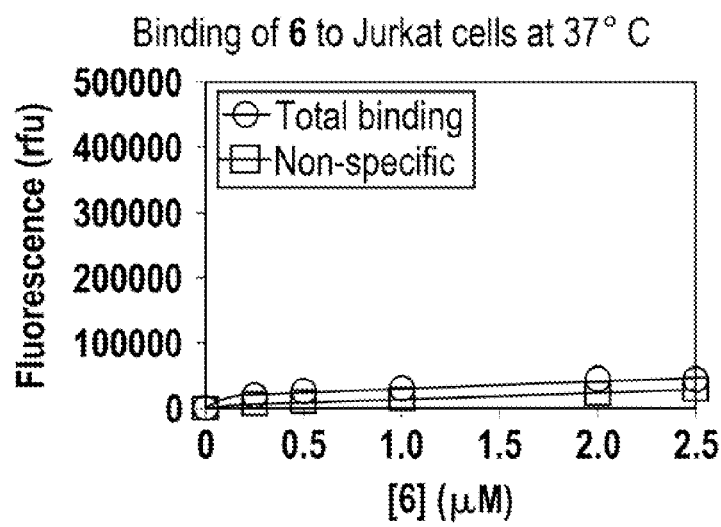
Figure 7D:
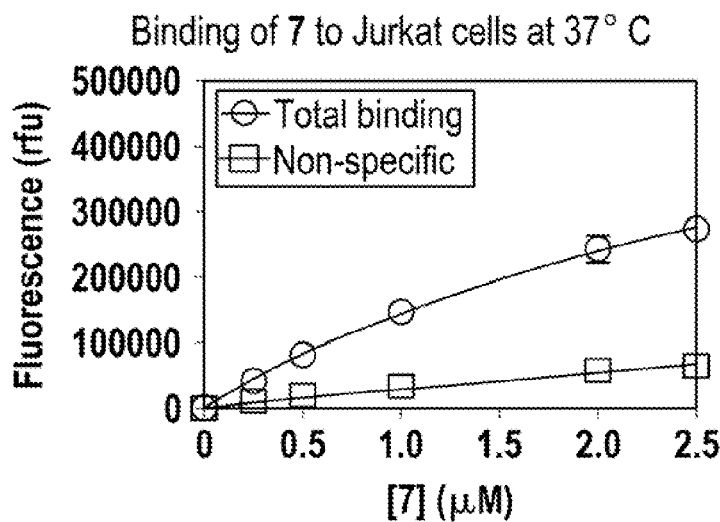
Figure 7E:
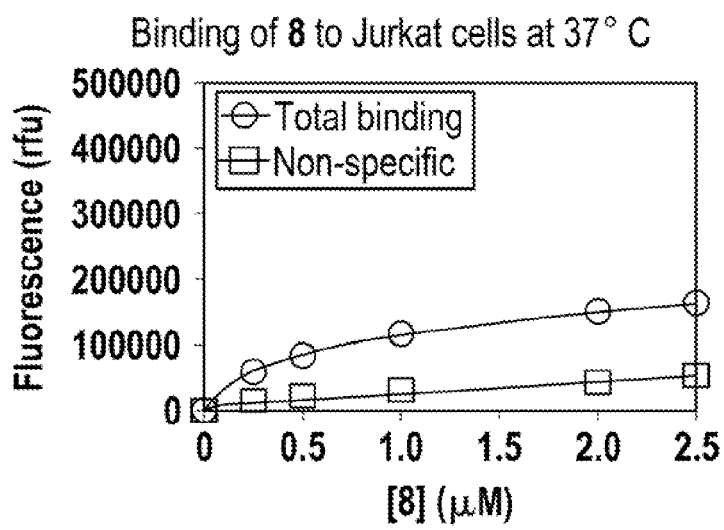
Figure 7F:
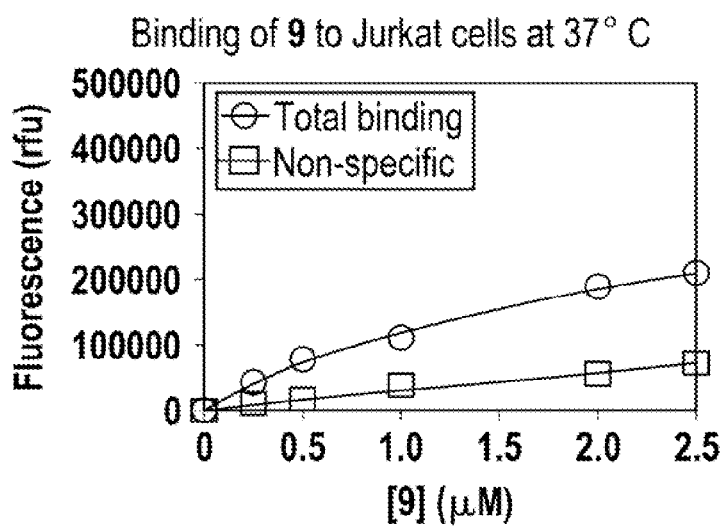
Figure 7G:
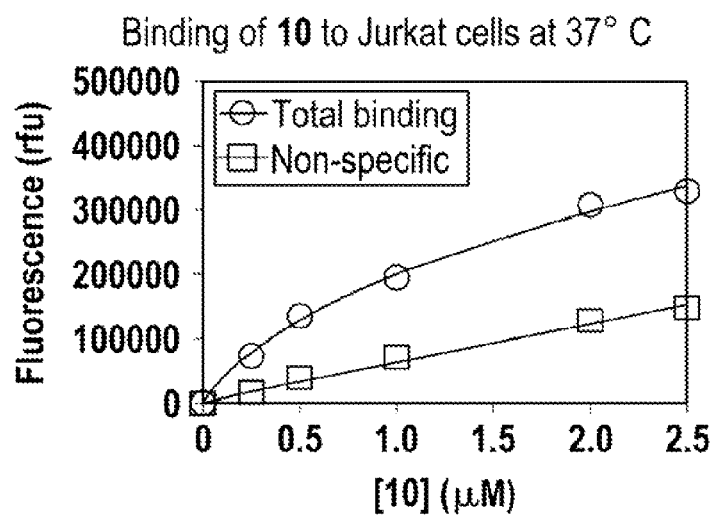
Figure 7H:
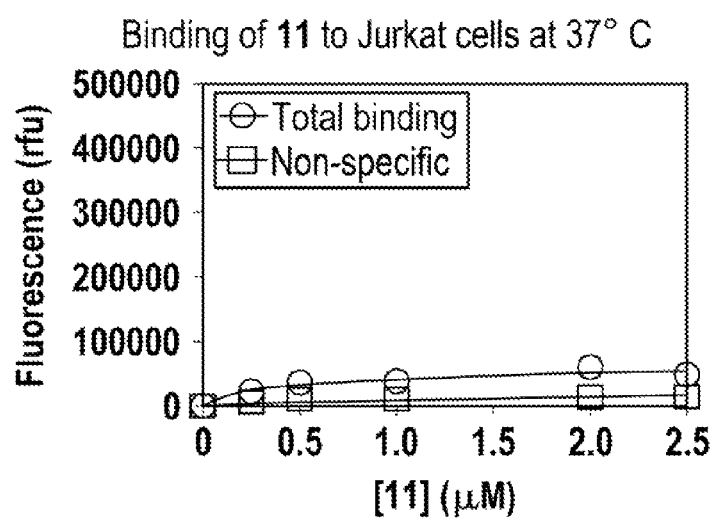
Figure 7I:
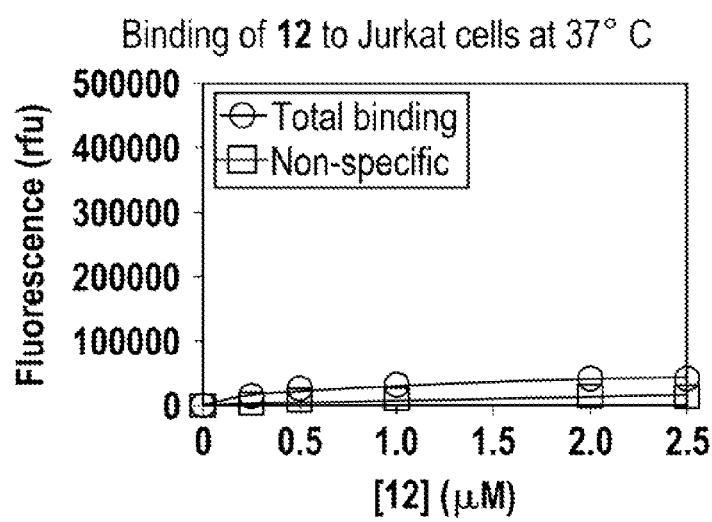
Figure 8:
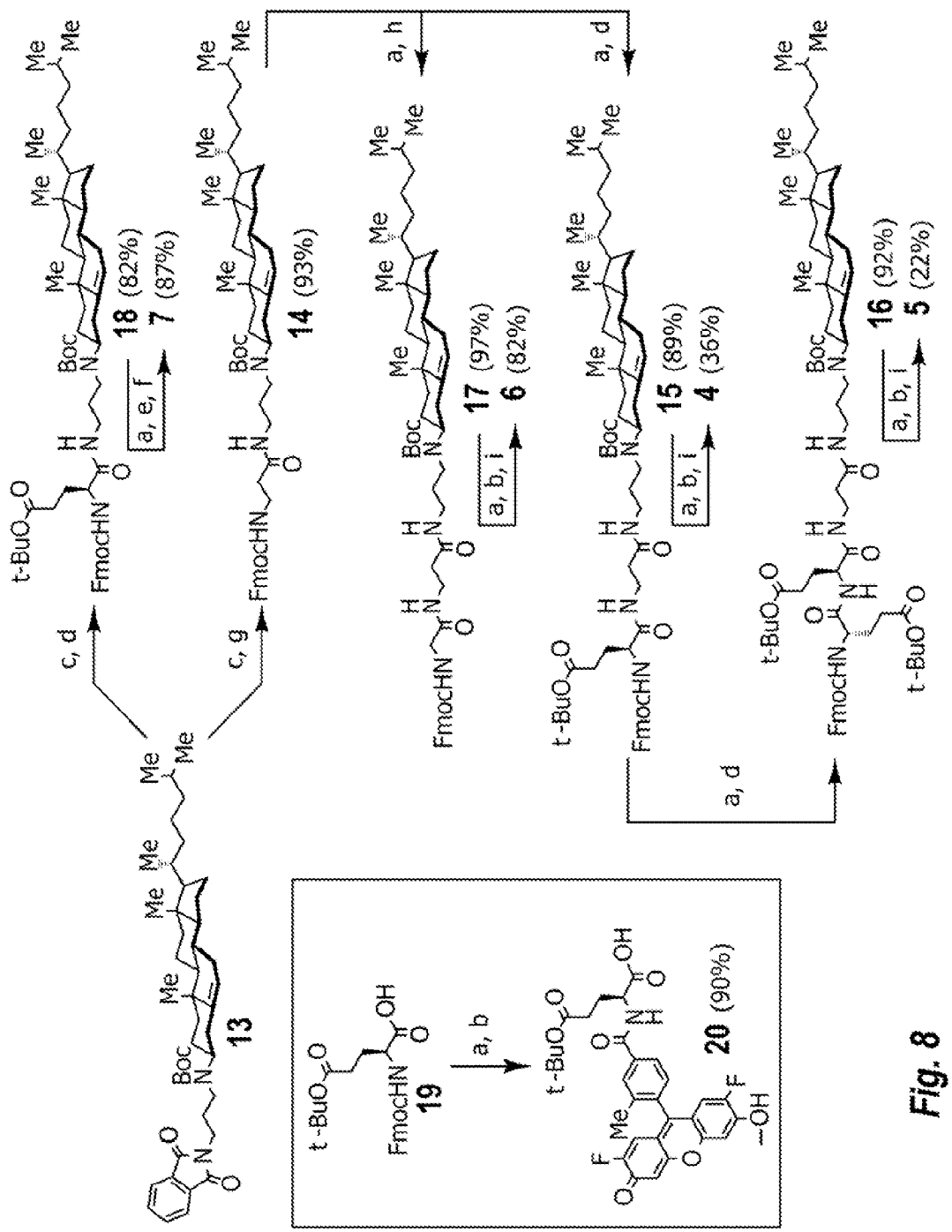
FIG. 8 includes a schematic representation of an embodiment of synthesis of compounds 4-7. Reagents and conditions include: step (a) Piperidine, DMF (1:4), 30 min; step (b) 4-Carboxy-Pennsylvania Green NHS Ester, DIEA, DMF, 16 h; step (c) H2NNH2, EtOH, 50° C., 4 h; step (d) EDC, HOBt, Fmoc-Glu(Ot-Bu)-OH, 4° C. to 22° C., 12 h; step (e) EDC, HOBt, compound 20, DMF, 12 h; step (f) TFA, CH2Cl2 (1:1), 2 h; step (g) EDC, HOBt, Fmoc-β-Ala-OH, 4° C. to 22° C., 12 h; step (h) EDC, HOBt, Fmoc-Gly-OH, 4° C. to 22° C., 12 h; and step (i) TFA, CH2Cl2 (1.5:8.5), 12 h.
Figure 9:
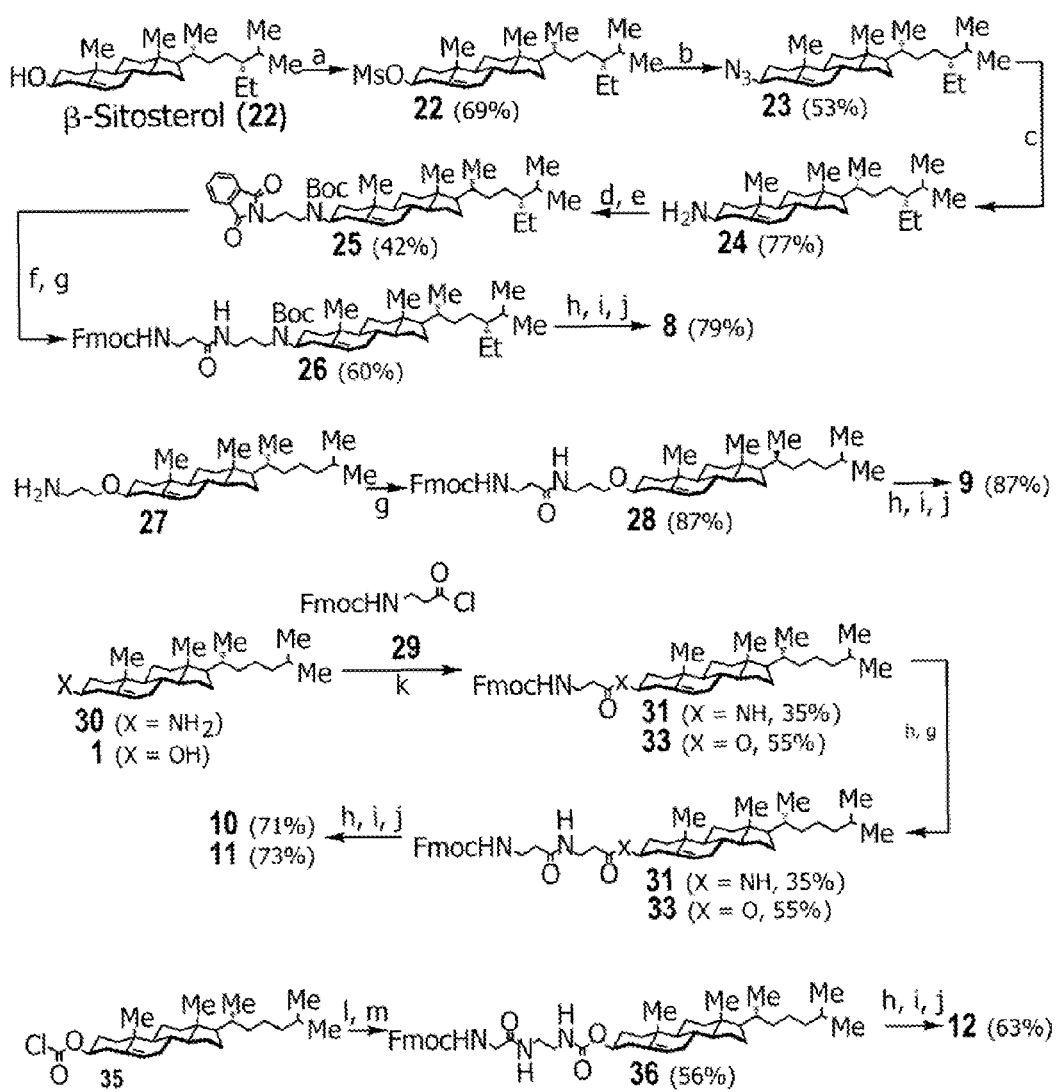
FIG. 9 includes a schematic representation of an embodiment of synthesis of compounds 8-12. Reagents and conditions include: step (a) MsCl, TEA, CH2Cl2, 4° C. to 22° C., 16 h; step (b) TMS-N3, BF3-OEt2, CH2Cl2, 16 h; step (c) LiAlH4, Et2O, CH2Cl2, 4° C. to 22° C., 2 h; step (d) N-3-bromopropylphthalimide, K2CO3, DMF, 60° C., 24 h; step (e) (Boc)2O, DIEA, CH2Cl2, 4 h; step (f) H2NNH2, EtOH, 50° C., 4 h; step (g) EDC, HOBt, Fmoc-β-Ala-OH, 4° C. to 22° C., 12 h; step (h) piperidine, DMF (1:4), 30 min; step (i) EDC, HOBt, compound 20, DMF, 12 h; step (j) TFA, CH2Cl2 (1:1), 2 h; step (k) DMAP, CH2Cl2, 30 min; step (l) excess ethylene diamine, CH2Cl2, 2 h; and step (m) EDC, HOBt, Fmoc-Gly-OH, 4° C. to 22° C., 12 h.

Using free cholesterol (compound 1, 200 μM, 10% DMSO) as a competitor, we quantified the relative affinities (Kd, app) and efficacies (Bmax) of compounds 4-12 in saturation binding experiments at both 16° C. (to limit endocytosis) and 37° C. (FIG. 4 and Table 1). These experiments confirmed the combined importance the N-alkyl substituent of cholesterylamine, an anionic functional group, and a spacer residue such as β-alanine to engender high affinity binding to cell surfaces and facilitate subsequent endocytosis.

Table 1 shows the relative affinity (Kd) and efficacy of binding (Bmax) of compounds 4-12 to Jurkat cells in media containing 10% FBS (a Ambiguous fit to binding model; b Not calculated due to low efficacy (Bmax<0.4×105)).

In summary, we identified structure-activity relationships that govern binding of fluorescent cholesterol mimics to the surface of living mammalian cells. New membrane anchor motifs of compounds 4 and 5 were identified that functionally mimic the recognition of cell surfaces by free cholesterol and that bind mammalian cells with high affinity/efficacy under physiologically relevant conditions including high concentrations of serum. These compounds have potential as useful probes of membrane biology and new tools for the delivery of impermeable molecules both in vitro and in vivo.

Doxorubicin

Figure 10:
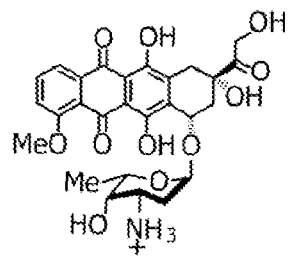
FIG. 10 illustrates the chemical structures of embodiments of cholesterylamine-linkers linked to doxorubicin as well as the structure of doxorubicin.
Figure 10:
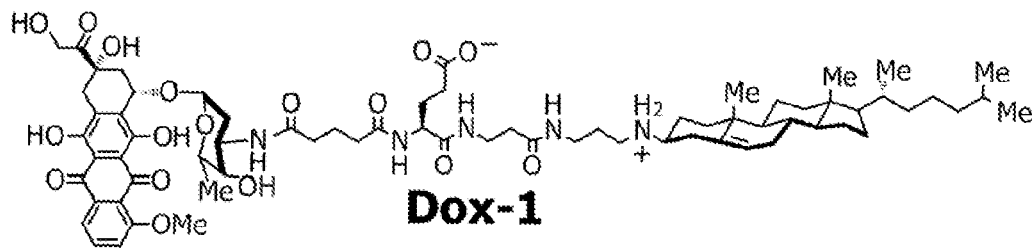
Figure 10:
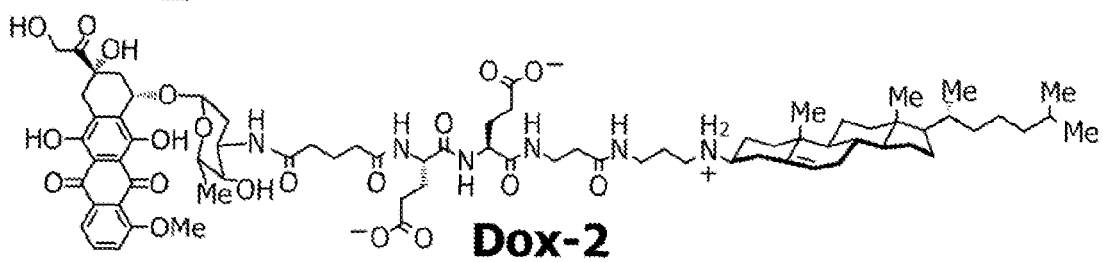
Figure 10:
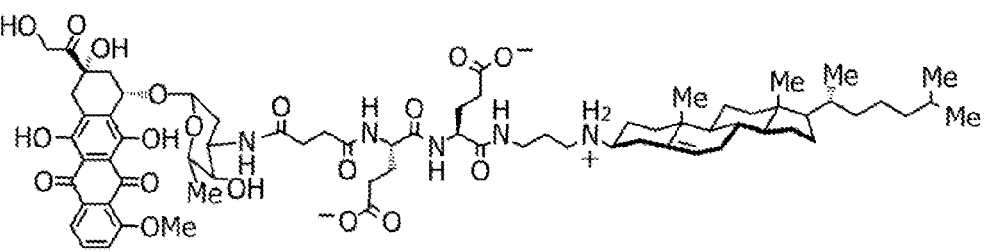
Figure 11:
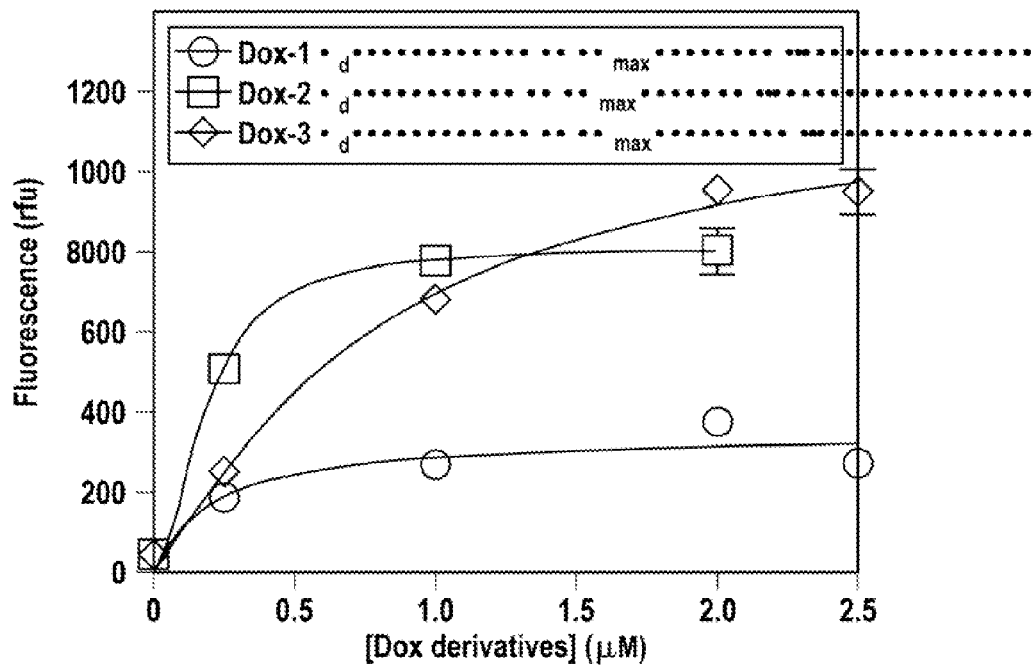
FIG. 11 includes a graph that illustrates specific binding of Dox-1, Dox-2, and Dox-3 of FIG. 10 to Jurkat cells at 37 degrees C.
Figure 12:
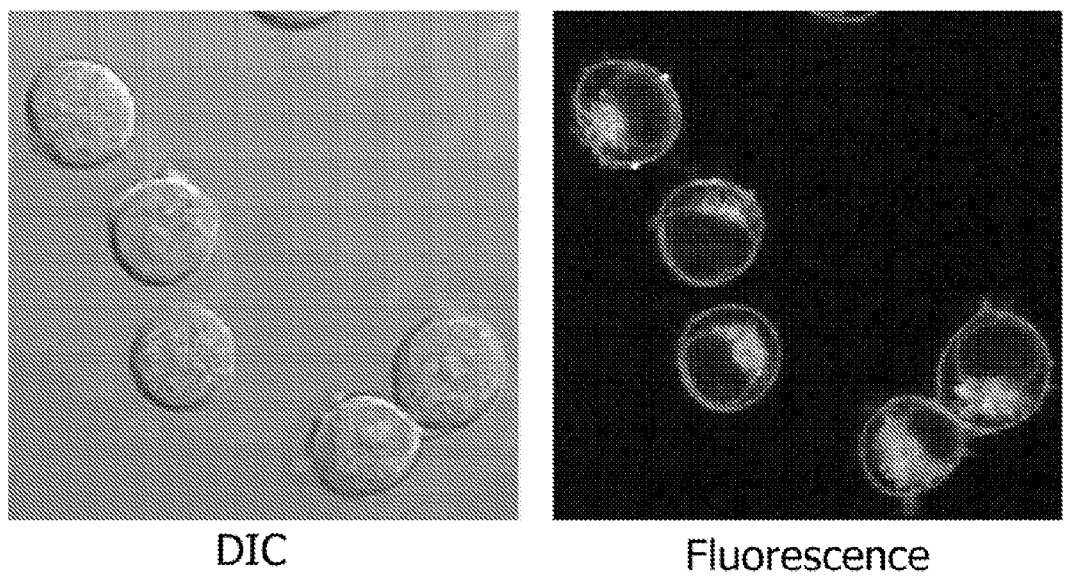
FIG. 12 includes micrographs that illustrates uptake of Dox-1 to Jurkat cells at 37 degrees C.

The cholesteryl-linker was coupled to doxorubixin (e.g., Dox-1, Dox-2, and Dox 3 as shown in FIG. 10) and tested for specific binding in Jurkat lymphocytes. Briefly, Specific binding of Dox-1, Dox-2, and Dox-3 to plasma membranes of Jurkat lymphocytes was studied by treatment for 5 min in media containing 10% serum at 37° C. Cholesterol (200 μM, 10% DMSO) was used as a specific competitor in saturation binding experiments, and a one-site with hill slope binding model was applied to generate the binding constants shown. Dox-1 was then studied by differential interference contrast (DIC) and confocal fluorescence micrographs. Jurkat lymphocytes treated with Dox-1 for 5 min at 37° C. These experiments revealed that the addition of a beta alanine linker subunit and glutamic acid residues enhances the affinity of doxorubicin-modified cholesterylamines for cellular plasma membranes.

Synthetic Procedures and Compound Characterization Data

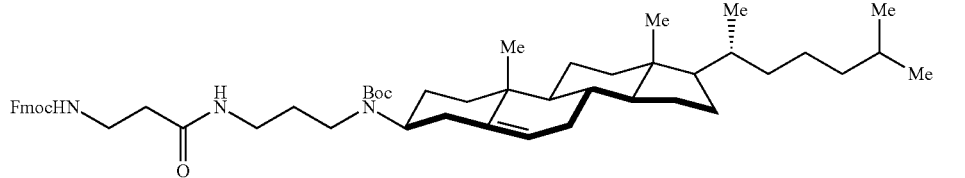

9H-Fluoren-9-ylmethyl{3-[(3-{(tert-butoxycarbonyl)[3β-cholest-5-en-3-yl]amino}propyl)amino]-3-oxopropyl}carbamate (compound 14)

To a solution of compound 13 (1.41 g, 2.1 mmol) in absolute ethanol (50 mL) was added anhydrous hydrazine (350 μL, 11 mmol). The solution was heated to 50° C. and stirred for 4 h. The reaction was cooled to 22° C., and a white precipitate was removed by filtration. The filtrate was concentrated in vacuo, and the residue was dissolved in CHCl3 (100 mL). After insoluble material was removed by filtration, concentration of the filtrate in vacuo afforded the phthalimide-deprotected primary amine (1.13 g, 99%), a white solid that was carried forward without further purification. To Fmoc-β-Ala-OH (715 mg, 2.3 mmol) in anhydrous CH2Cl2 (50 mL) at 4° C. was added HOBt (340 mg, 2.5 mmol) and EDC (480 mg, 2.5 mmol). This mixture was stirred at 4° C. for 30 min. The phthalimide-deprotected primary amine in anhydrous CH2Cl2 (25 mL) was added dropwise, the reaction was allowed to warm to 22° C. and was further stirred for 12 h. The solution was diluted with CH2Cl2 (100 mL) and washed with aqueous NaOH (0.1M, 100 mL) followed by saturated aqueous NaCl (100 mL). The organic layer was dried over anhydrous Na2SO4 and concentrated in vacuo. Flash column chromatography (hexanes, ethyl acetate, 2:1) afforded compound 14 (1.62 g, 93%) as a glassy solid, mp 84-86° C.; 1H NMR (400 MHz, CDCl3) δ 7.76 (d, J=7.3 Hz, 2H), 7.58 (d, J=7.4 Hz, 2H), 7.39 (m, 2H), 7.30 (m, 2H), 7.05 (br, 1H), 5.82 (br, 1H), 5.33 (s, 1H), 4.34 (d, J=7.2 Hz, 2H), 4.22 (t, J=6.8 Hz, 1H), 3.51-3.24 (m, 6H), 2.60-0.86 (m, 54H), 0.67 (s, 3H); 13C NMR (100 MHz, CDCl3) δ 172.0, 156.5, 144.0, 143.9, 141.2, 127.6, 127.6, 127.0, 125.1, 125.0, 121.4, 119.9, 77.1, 66.7, 56.7, 56.1, 50.0, 47.2, 42.3, 39.7, 39.5, 37.2, 36.8, 36.5, 36.1, 35.9, 35.7, 31.8, 28.5, 28.2, 27.9, 26.8, 24.2, 23.8, 22.8, 22.5, 20.9, 19.4, 18.7, 11.8; IR (film) v max 3323, 2949, 1717, 1668, 1539, 1449, 1412, 1366, 1251, 1169, 1081, 908, 737 cm-1; HRMS (ESI+) m/z 835.5819 (M+H+, C53H78N3O5 requires 835.5863).

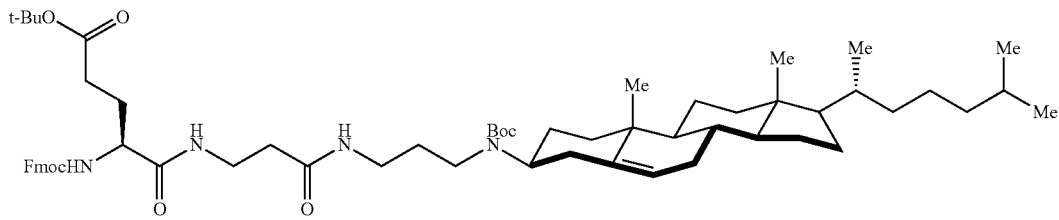

tert-Butyl-(15S)-5-[3β-cholest-5-en-3-yl]-15-{[(9H-fluoren-9-ylmethoxy)carbonyl]amino}-2,2-dimethyl-4,10,14-trioxo-3-oxa-5,9,13-triazaoctadecan-18-oate (compound 15)

Compound 14 (303 mg, 0.36 mmol) was added to DMF (2 mL) containing piperidine (20%) and stirred for 30 min at 22° C. The solvent was removed in vacuo to afford the crude primary amine. To a solution of Fmoc-Glu (t-Bu)-OH (157 mg, 0.37 mmol) in anhydrous CH2Cl2 (10 mL) at 4° C. were added HOBt (55 mg, 0.41 mmol) and EDC (79 mg, 0.41 mmol) and the solution was stirred for 30 min. To this solution was added the crude primary amine derived from 14 dissolved in anhydrous CH2Cl2 (5 mL). The reaction was allowed to warm to 22° C. and stirred for 12 h. This solution was diluted with CH2Cl2 (30 mL) and washed with aqueous NaOH (0.1M, 30 mL) followed by saturated aqueous NaCl (30 mL). The organic layer was dried over anhydrous Na2SO4 and concentrated in vacuo. Flash column chromatography (CH2Cl2, MeOH, 50:1) afforded compound 15 (361 mg, 98%) as a white solid, mp 120-122° C.; 1H NMR (400 MHz, CDCl3) δ 7.76 (d, J=7.5 Hz, 2H), 7.60 (d, J=7.5 Hz, 2H), 7.51 (br, 1H), 7.39 (t, J=7.5 Hz, 2H), 7.31 (t, J=7.5 Hz, 2H), 7.09 (br, 1H), 5.88 (d, J=8.0 Hz, 1H), 5.31 (d, J=4.0 Hz, 1H), 4.34 (t, J=7.1 Hz, 2H), 4.21 (t, J=7.1 Hz, 2H), 3.57-3.16 (m, 6H), 2.60-0.85 (m, 67H), 0.66 (s, 3H); 13C NMR (100 MHz, CDCl3) δ 172.7, 171.4, 171.4, 156.2, 143.9, 143.8, 141.3, 127.7, 127.9, 125.2, 121.4, 119.9, 80.9, 79.9, 67.1, 56.7, 56.1, 54.6, 50.1, 47.2, 42.3, 39.7, 39.8, 39.6, 38.4, 37.1, 36.7, 36.2, 36.0, 35.8, 31.9, 31.5, 28.6, 28.2, 28.1, 28.0, 27.9, 27.0, 24.3, 23.8, 22.8, 22.6, 21.0, 19.5, 18.7, 11.8; IR (film) ν max 3295, 3066, 3005, 2935, 2863, 1726, 1652, 1540, 1465, 1451, 1415, 1366, 12523, 1163, 1046, 849, 757, 666 cm-1; HRMS (ESI+) m/z 1043.6853 (M+Na+, C62H92N4O8Na requires 1043.6813).

(4S)-5-{[3-({3-[3β-Cholest-5-en-3-ylamino] propyl}amino)-3-oxopropyl]amino}-4-{[4-(2,7-difluoro-6-hydroxy-3-oxo-3H-xanthen-9-yl)-3-methylbenzoyl]amino}-5-oxopentanoic acid (compound 4)

Compound 15 (75 mg, 0.074 mmol) was added to DMF (1 mL) containing piperidine (20%) and stirred for 30 min at 22° C. The solvent was removed in vacuo to afford the crude primary amine. The resulting residue was dissolved in anhydrous DMF (5 mL), 4-carboxy-Pennsylvania Green succinimidyl ester (30 mg, 0.062 mmol) was added, followed by diisopropylethylamine (DIEA, 50 μL, 0.24 mmol). The reaction was stirred at 22° C. for 12 h and concentrated in vacuo. To the resulting orange residue was added CH2Cl2 (5 mL) containing TFA (15%) and the solution was stirred at 22° C. for 12 h. The reaction was concentrated in vacuo, the crude product was dissolved in methanol (2 mL), and the product was purified by preparative reverse-phase HPLC (gradient: 90% H2O, 9.9% MeCN, and 0.1% TFA to 99.9% MeCN and 0.1% TFA over 20 min; retention time=15.4 min (495 nm) to afford compound 4 (23 mg, 36.4%) as an orange solid, mp 196-198° C.; 1H NMR (300 MHz, DMSO-d6) δ 8.76-8.72 (m, 3H), 8.19 (s, 2H), 8.14 (s, 1H), 8.05 (d, J=5.4 Hz, 1H), 7.49 (d, J=5.7 Hz, 1H), 6.98 (s, 2H), 6.72 (d, J=8.2 Hz, 2H), 5.45 (s, 1H), 4.53 (d, J=2.7 Hz, 1H), 3.23 (m, 2H), 3.14 (m, 2H), 3.01 (m, 3H), 2.46-0.92 (m, 51H), 0.72 (s, 3H); 13C NMR (75 MHz, DMSO-d6) δ 174.0, 172.7, 171.2, 170.8, 165.9, 158.0, 149.3, 138.6, 135.9, 135.2, 134.5, 129.8, 129.0, 125.5, 122.4, 105.2, 56.6, 56.1, 55.5, 53.1, 49.3, 41.8, 41.6, 36.4, 36.2, 35.6, 35.3, 35.2, 34.3, 31.2, 30.5, 27.7, 27.4, 26.9, 26.2, 24.3, 23.8, 23.2, 22.6, 22.4, 20.5, 19.2, 18.7, 18.5, 11.6; IR (film) ν max 3324, 3071, 2950, 2863, 1671, 1646, 1610, 1539, 1503, 1465, 1373, 1310, 1193, 1136, 836, 759 cm-1; HRMS (ESI+) m/z 1007.5679 (M+H+, C59H77F2N4O8Na requires 1007.5710).

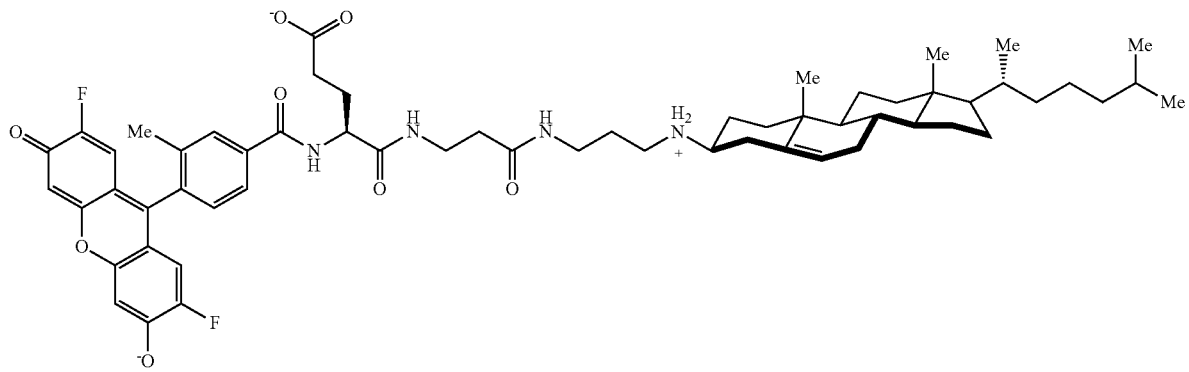

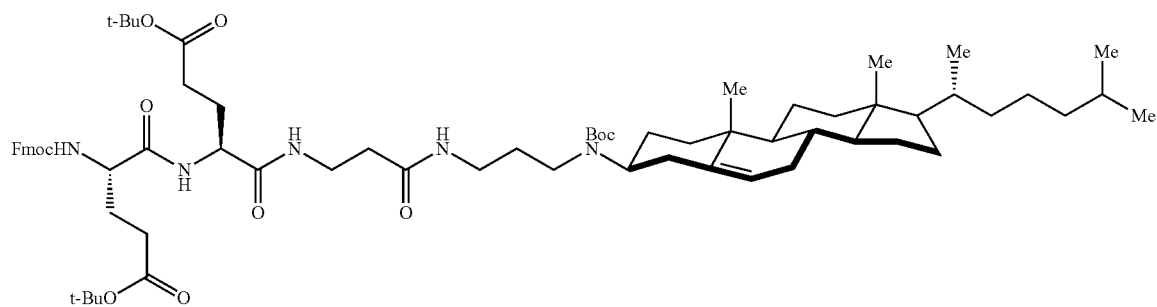

16 tert-Butyl (15S,18S)-15-(3-tert-butoxy-3-oxopropyl)-5-[3β-cholest-5-en-3-yl]-18-{[(9H-fluoren-9-ylmethoxy)carbonyl]amino}-2,2-dimethyl-4,10,14,17-tetraoxo-3-oxa-5,9,13,16-tetraazahenicosan-21-oate (compound 16)

Compound 15 (150 mg, 0.15 mmol) was added to DMF (2 mL) containing piperidine (20%) and stirred for 30 min at 22° C. The solvent was removed in vacuo to afford the crude primary amine. To Fmoc-Glu(t-Bu)-OH (70 mg, 0.16 mmol) in anhydrous CH2Cl2 (10 mL) at 4° C. was added HOBt (24 mg, 0.18 mmol) and EDC (35 mg, 0.18 mmol) and the solution was stirred for 30 min. The crude primary amine derived from 15 in anhydrous CH2Cl2 (5 mL) was added. The reaction was allowed to warm to 22° C. and stirred for 12 h. This solution was diluted with CH2Cl2 (30 mL) and washed with aqueous NaOH (0.1 M, 30 mL) followed by saturated aqueous NaCl (30 mL). The organic layer was dried over anhydrous Na2SO4 and concentrated in vacuo. Flash column chromatography (CH2Cl2, MeOH, 30:1) afforded compound 16 (162 mg, 92%) as a white solid, mp 138-144° C.; 1H NMR (400 MHz, CDCl3) δ 7.78 (d, J=7.5 Hz, 2H), 7.63 (d, J=7.2 Hz, 2H), 7.59 (br, 1H), 7.41 (t, J=7.4 Hz, 2H), 7.36 (br, 1H), 7.33 (t, J=7.4 Hz, 2H), 7.19 (br, 1H), 5.92 (br, 1H), 5.32 (d, J=6.4 Hz, 1H), 4.36 (d, J=7.2 Hz, 3H), 4.24 (t, J=7.0 Hz, 2H), 3.58-3.20 (br, 7H), 2.60-0.86 (m, 79H), 0.67 (s, 3H); 13C NMR (100 MHz, CDCl3) δ 172.9, 172.8, 171.4, 171.1, 156.3, 156.3, 143.9, 143.7, 141.2, 127.7, 127.1, 125.2, 121.3, 120.0, 81.0, 80.9, 77.2, 67.2, 56.7, 56.2, 53.1, 50.1, 47.1, 42.3, 39.8, 39.5, 38.4, 36.7, 36.2, 35.8, 31.9, 28.6, 28.2, 28.0, 27.9, 24.3, 23.8, 22.8, 22.6, 21.0, 19.5, 18.7, 11.8; IR (film) ν max 3289, 3066, 3005, 2934, 2868, 1729, 1693, 1679, 1636, 1539, 1450, 1413, 1388, 1367, 1281, 1254, 1158, 1044, 757, 667 cm-1; HRMS (ESI+) m/z 1206.8032 (M+H+, C71H108N5O11 requires 1206.8045).

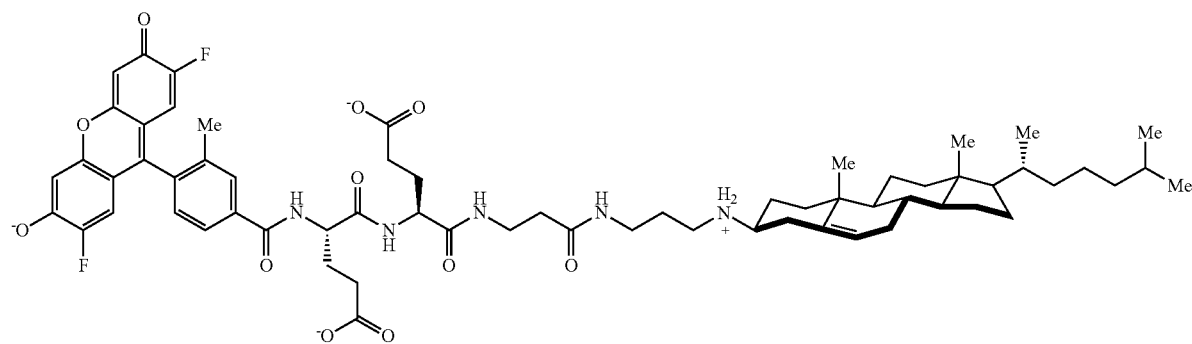

5

(4S)-5-{[(1S)-3-Carboxy-1-({[3-({3-[3β-cholest-5-en-3-ylamino]propyl}amino)-3-oxopropyl]amino}carbonyl)propyl]amino}-4-{[4-(2,7-difluoro-6-hydroxy-3-oxo-3H-xanthen-9-yl)-3-methylbenzoyl]amino}-5-oxopentanoic acid (compound 5)

Compound 16 (30 mg, 0.025 mmol) was added to DMF (1 mL) containing piperidine (20%) and stirred for 30 min at 22° C. The solvent was removed in vacuo to afford the crude primary amine. To the resulting residue in dry DMF (2 mL) was added 4-carboxy-Pennsylvania Green succinimidyl ester [Mottram, 2007 #1675] (13 mg, 0.027 mmol) followed by diisopropylethylamine (50 μL, 0.24 mmol). The reaction was stirred at 22° C. for 12 h and concentrated in vacuo. The orange residue was treated with CH2Cl2 (5 mL) containing TFA (15%) and stirred at 22° C. for 12 h. The reaction was concentrated in vacuo, and the crude product was dissolved in methanol (2 mL) and purified by preparative reverse-phase HPLC (gradient: 90% H2O, 9.9% MeCN, and 0.1% TFA to 99.9% MeCN and 0.1% TFA over 15 min; retention time=13.5 min (495 nm) to afford compound 5 (6.2 mg, 22%) as an orange solid, mp 145-148° C.; 1H NMR (400 MHz, DMSO-d6) δ 8.65 (d, J=7.8 Hz, 1H), 8.37 (s, 2H), 8.07-7.92 (m, 4H), 7.39 (d, J=8.0 Hz, 1H), 6.85 (s, 1H), 6.62 (d, J=10.9 Hz, 1H), 5.37 (s, 1H), 4.46 (m, 1H), 4.21 (m, 1H), 3.29-3.20 (m, 4H), 2.90 (m, 3H), 2.46-0.92 (m, 55H), 0.63 (s, 3H); 13C NMR (100 MHz, DMSO-d6) δ 174.4, 172.6, 171.8, 171.7, 129.8, 129.0, 125.5, 122.4, 105.2, 57.0, 56.5, 56.0, 49.8, 42.3, 42.1, 39.3, 39.2, 39.1, 36.8, 36.6, 36.1, 36.0, 35.8, 35.6, 33.8, 31.7, 31.0, 30.6, 27.9, 25.8, 24.9, 24.8, 24.3, 23.6, 23.1, 22.8, 19.5, 19.2, 19.0, 12.1; IR (film) ν max 3419, 2951, 1682, 1643, 1540, 1438, 1375, 1310, 1205, 1142, 1015, 801, 721.6 cm$^{-1}$; HRMS (ESI+) m/z 1136.6179 (M+H+, $C_{64}H_{84}F_2N_5O_{11}$ requires 1136.6136).

compound 17 (153 mg, 97%) as a white solid, mp 112-114° C.; $^1$H NMR (400 MHz, CDCl$_3$) δ 7.75 (d, J=7.4 Hz, 2H), 7.60 (d, J=7.0 Hz, 2H), 7.39 (t, J=7.3 Hz, 2H), 7.30 (t, J=7.3 Hz, 2H), 6.99 (br, 1H), 5.78 (br, 1H), 5.31 (s, 1H), 4.38 (d, J=6.9 Hz, 2H), 4.22 (t, J=7.0 Hz, 1H), 3.86 (d, J=4.5 Hz, 2H), 3.56 (d, J=5.0 Hz, 2H), 3.22 (m, 2H), 2.52-0.86 (m, 56H), 0.67 (s, 3H); $^{13}$C NMR (100 MHz, CDCl$_3$) δ 171.5, 169.0, 156.5, 148.3, 143.8, 141.2, 127.7, 127.0, 125.1, 121.4, 119.9, 80.0, 67.1, 56.7, 56.1, 50.0, 47.1, 44.3, 42.3, 41.5, 39.7, 39.5, 38.4, 37.1, 36.7, 36.1, 35.9, 35.7, 31.8, 28.5, 28.2, 27.9, 26.8, 24.2, 23.8, 22.8, 22.5, 20.9, 19.4, 18.7, 11.8; IR (film) ν max 3311, 2936, 2868, 1717, 1667, 1543, 1465, 1450, 1413, 1365, 1249, 1168, 1048, 758 cm$^{-1}$; HRMS (ESI+) m/z 893.6122 (M+H+, $C_{55}H_{81}N_4O_6$ requires 893.6156).

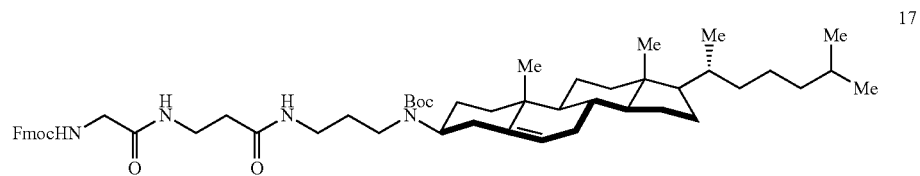

tert-Butyl-3β-cholest-5-en-3-yl[14-(9H-fluoren-9-yl)-5,9,12-trioxo-13-oxa-4,8,11-triazatetradec-1-yl]carbamate (compound 17)

Compound 14 (150 mg, 0.18 mmol) was added to DMF (2 mL) containing piperidine (20%) and stirred for 30 min at 22° C. The solvent was removed in vacuo to afford the crude primary amine. To a solution of Fmoc-Gly-OH (60 mg, 0.20 mmol) in anhydrous CH$_2$Cl$_2$ (10 mL) at 4° C. were added HOBt (30 mg, 0.22 mmol) and EDC (42 mg, 0.22 mmol) and the solution was stirred for 30 min. The primary amine derived from compound 14 in anhydrous CH$_2$Cl$_2$ (5 mL) was added. The reaction was allowed to warm to 22° C. and stirred for 12 h. This solution was diluted with CH$_2$Cl$_2$ (30 mL) and washed with aqueous NaOH (0.1 M, 30 mL) followed by saturated aqueous NaCl (30 mL). The organic layer was dried over anhydrous Na$_2$SO$_4$ and concentrated in vacuo. Flash column chromatography (CH$_2$Cl$_2$, MeOH, 20:1) afforded

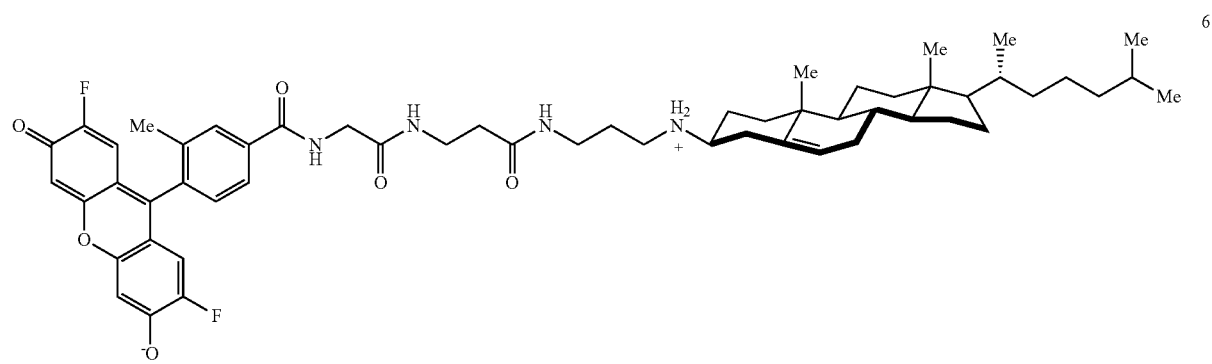

N-(2-{[3-({3-[3β-Cholest-5-en-3-ylamino]propyl}amino)-3-oxopropyl]amino}-2-oxoethyl)-4-(2,7-difluoro-6-hydroxy-3-oxo-3H-xanthen-9-yl)-3-methylbenzamide (compound 6)

Compound 17 (25 mg, 0.028 mmol) was added to DMF (1 mL) containing piperidine (20%) and stirred for 30 min at 22° C. The solvent was removed in vacuo to afford the crude primary amine. To the resulting residue in dry DMF (2 mL) was added 4-carboxy-Pennsylvania Green succinimidyl ester [Mottram, 2007 #1675] (11 mg, 0.023 mmol) followed by diisopropylethylamine (50 μL, 0.24 mmol). The reaction was stirred at 22° C. for 12 h and concentrated in vacuo. The orange residue was treated with CH2Cl2 (5 mL) containing TFA (15%) and stirred at 22° C. for 12 h. The reaction was concentrated in vacuo, and the crude product was dissolved in methanol (2 mL) and purified by preparative reverse-phase HPLC (gradient: 90% H2O, 9.9% MeCN, and 0.1% TFA to 99.9% MeCN and 0.1% TFA over 15 min; retention time=13.0 min (495 nm) to afford compound 6 (18 mg, 82%) as an orange solid, mp 200-203° C.; 1H NMR (300 MHz, DMSO-d6) δ 8.91 (s, 1H), 8.56 (s, 2H), 8.0-7.91 (m, 4H), 7.40 (d, J=7.6 Hz, 1H), 6.86 (s, 2H), 6.60 (d, J=11.1 Hz, 2H), 5.38 (s, 1H), 3.87 (m, 2H), 3.14 (m, 4H), 2.93 (m, 3H), 2.30-0.85 (m, 47H), 0.61 (s, 3H); 13C NMR (75 MHz, DMSO-d6) δ 170.9, 168.8, 166.0, 149.0, 138.5, 136.0, 135.2, 134.8, 129.9, 129.0, 125.3, 122.6, 105.0, 56.5, 56.1, 55.5, 49.3, 42.7, 41.7, 41.5, 36.1, 35.9, 35.6, 35.4, 35.2, 34.2, 31.2, 27.7, 27.4, 26.2, 26.1, 24.4, 23.2, 22.7, 22.4, 20.5, 19.2, 18.7, 18.5, 11.6; IR (film) v max 3419, 2950, 2115, 1646, 1540, 1465, 1374, 1310,

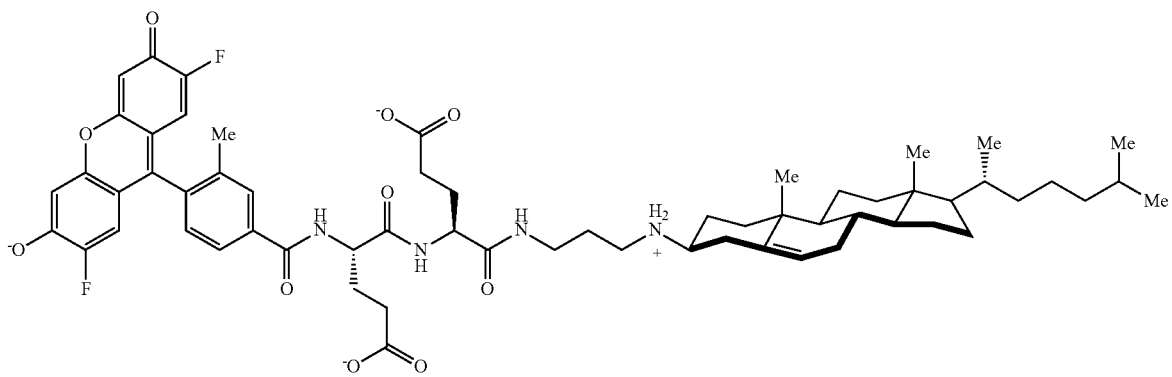

7

1194, 1147, 1016, 875 cm-1; HRMS (ESI+) m/z 957.5350 (M+Na+, C56H72F2N4O6Na requires 957.5350).

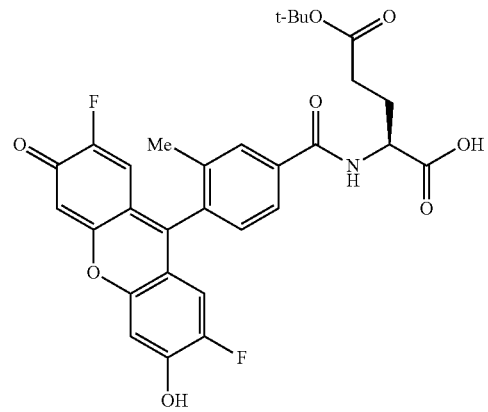

5-(tert-butoxy)-2-(4-(2,7-difluoro-6-hydroxy-3-oxo-3H-xanthen-9-yl)-3-methylbenzamido)-5-oxopentanoic acid (compound 20)

Fmoc-Glu(O-t-Bu)-OH (compound 19, 67 mg, 0.156 mmol) was treated with piperidine (20%) in DMF (1 mL) for 30 min. The solvent was removed in vacuo to afford the crude primary amine. A solution of 4-carboxy-Pennsylvania Green succinimidyl ester3 (25 mg, 0.052 mmol) in DMF (1 mL) was added to the crude primary amine in DMF (1 mL) followed by DIEA (0.25 mL). The reaction was allowed to stir at 22° C. for 16 h, dried in vacuo, and purified by flash column chromatography (MeOH, CH2Cl2, AcOH, 5:94.9:0.1) to afford compound 20 (27 mg, 90%) as an orange residue, mp 134-138° C.; 1H NMR (400 MHz, CD3OD) δ 8.00 (s, 1H), 7.94 (dd, J=7.9, 1.2 Hz, 1H), 7.40 (d, J=7.9 Hz, 1H), 6.98-6.89 (m, 2H), 6.81-6.77 (m, 2H), 4.70 (dd, J=9.6, 4.9 Hz, 1H), 2.47 (t, J=7.0 Hz, 2H), 2.39-2.27 (m, 1H), 2.14-2.08 (m, 1H), 2.12 (s, 3H), 1.46 (s, 9H); 13C NMR (101 MHz, CD3OD) δ 174.95, 173.97, 169.66, 156.19, 138.02, 137.15, 136.55, 131.01, 130.47, 126.62, 112.98, 112.76, 106.32, 81.94, 53.70, 32.95, 28.35 (t), 27.66, 19.60; IR (film) v max 2929, 1678, 1607, 1536, 1371, 1302, 1190, 1139, 953, 842, 801, 750, 724 cm-1; HRMS (ESI+) m/z 568.1779 (M+H+, C30H27F2NO8, requires 568.1705).

(4S)-5-(((2S)-4-carboxy-1-((3-[3β-cholest-5-en-3-ylamino]propyl)amino)-1-oxobutan-2-yl)amino)-4-(4-(2,7-difluoro-6-hydroxy-3-oxo-3H-xanthen-9-yl)-3-methylbenzamido)-5-oxopentanoic acid (compound 7)

Compound 18, synthesized by a previously reported method, 4 (26.8 mg, 0.028 mmol) was added to DMF (0.5 mL) containing piperidine (20%) and stirred for 30 min at 22° C. The solvent was removed in vacuo to afford the crude primary amine. To a solution of compound 20 (8.0 mg, 0.014 mmol) in anhydrous DMF (2 mL) at 4° C. was added HOBt (4.0 mg, 0.028 mmol) and EDC (5.4 mg, 0.028 mmol) and the solution was stirred at 22° C. for 30 min. The primary amine derived from compound 18 in anhydrous DMF (1 mL) was added at 4° C. The reaction was allowed to warm to 22° C. and stirred for 12 h. The reaction was concentrated in vacuo. The resulting residue was re-dissolved in TFA/CH2Cl2 (1:1, 2 mL) and stirred at 22° C. for 2 h. The solvent was removed in vacuo, the crude product was dissolved in DMSO (2 mL), and purified by preparative reverse-phase HPLC (gradient: 90% H2O, 9.9% MeCN, and 0.1% TFA to 99.9% MeCN and 0.1% TFA over 20 min; retention time=16.5 min (495 nm) to afford compound 7 (13.1 mg, 87%) as a orange solid, mp 175-178° C.; 1H NMR (500 MHz, CD3OD) δ 7.93 (s, 1H), 7.87-7.84 (m, 1H), 7.45 (t, J=7.5 Hz, 1H), 6.87-6.75 (m, 2H), 6.72-6.58 (m, 2H), 5.39 (d, J=4.9 Hz, 1H), 4.45 (m, 1H), 4.19 (m, 1H), 3.37-3.28 (m, 2H), 3.28-3.23 (m, 2H), 3.03-2.94 (m, 2H), 2.88 (m, 1H), 2.54-0.69 (m, 52H), 0.59 (s, 3H); 13C NMR (126 MHz, CD3OD) δ 176.85, 176.47, 174.94, 174.34, 169.92, 156.15, 146.38, 140.74, 139.53, 138.09, 136.70, 131.60, 131.47, 131.15, 130.50, 130.09, 126.78 (d, J=13.6 Hz), 124.85 (d, J=4.8 Hz), 122.22, 115.64, 113.74, 106.42, 59.41, 58.03, 57.51, 55.76, 55.01, 51.42, 43.35 (d, J=22.4 Hz), 40.99, 40.69, 38.22, 37.82, 37.35, 37.10, 36.92, 36.38, 32.99 (d, J=14.1 Hz), 31.55, 31.23, 29.22 (d, J=14.1 Hz), 27.82, 27.67, 27.58, 26.27, 25.98, 25.24, 24.96, 23.08 (d, J=31.7 Hz), 22.06, 19.64 (d, J=10.6 Hz), 19.22, 12.27; IR (film) v max 3387, 2323, 1675, 1541, 1439, 1202, 1135, 842, 802, 724 cm-1; HRMS (ESI−) m/z 1064.5603 (M−, C61H78F2N4O10 requires 1064.5686).

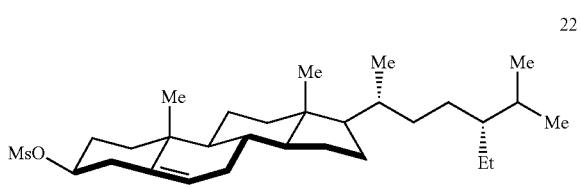

22

Sitost-5-en-3β-ol, methanesulfonate (compound 22)

To a solution of β-sitosterol (compound 21, 5.0 g, 12.0 mmol) in anhydrous $CH_2Cl_2$ (100 mL) at 4° C. was added freshly distilled triethylamine (2.7 mL, 18.1 mmol) followed by a dropwise solution of methanesulfonyl chloride (1.03 mL, 13.25 mmol) in anhydrous $CH_2Cl_2$ (10 mL). The reaction was maintained at 4° C. for 30 min, warmed to 22° C., and stirred for 16 h. The reaction was concentrated in vacuo and the resulting residue was purified by flash chromatography (ethyl acetate, hexane, 1:4) to give compound 22 (4.1 g, 69%) as a white solid, mp 97-100° C.; $^1$H NMR (400 MHz, CDCl$_3$) δ 5.45-5.38 (m, 1H), 4.52 (dt, J=11.9, 3.7 Hz, 1H), 2.99 (s, 3H), 2.51 (ddd, J=7.2, 4.9, 2.0 Hz, 2H), 2.09-0.75 (m, 42H), 0.68 (s, 3H). $^{13}$C NMR (101 MHz, CDCl$_3$) δ 138.57, 123.61, 81.82, 56.52, 55.96, 49.86, 45.76, 42.19, 39.55, 39.04, 38.62, 36.79, 36.25, 35.97, 33.84, 31.71 (d, J=5.5 Hz), 29.12, 28.85, 28.04, 26.09, 24.11, 22.98, 20.89, 19.62, 18.96 (d, J=9.6 Hz), 18.63, 11.75 (d, J=13.3 Hz); IR (film) v max 2958, 2931, 2867, 1465, 1350, 1326, 1168, 946, 865, 802 cm$^{-1}$; HRMS (EI+) m/z 492.9897 (M+, C$_{30}$H$_{52}$O$_3$S requires 492.3637).

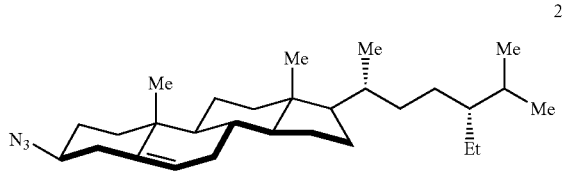

23

3β-Azido-5-sitostene (compound 23)

To a solution of compound 22 (1.7 g, 3.45 mmol) in anhydrous $CH_2Cl_2$ (30 mL) was added TMS-N$_3$ (0.68 mL, 5.20 mmol), followed by BF$_3$.Et$_2$O (0.86 mL, 6.90 mmol). The reaction was stirred at 22° C. for 16 h. The reaction was slowly poured into aqueous NaOH (1.0 M, 30 mL) and stirred for 5 min. The organic phase was separated and the aqueous layer was extracted with $CH_2Cl_2$ (30 mL). The combined organic extracts were washed with saturated NaCl solution (500 mL), dried over anhydrous Na$_2$SO$_4$, and concentrated in vacuo to give the crude product as light yellow oil. The crude product was purified by flash column chromatography (ethyl acetate, hexane, 2:98) to afforded compound 23 (800 mg, 53%) as a white solid, mp 74-78° C.; $^1$H NMR (400 MHz, CDCl$_3$) δ 5.42-5.35 (m, 1H), 3.20 (tdd, J=11.5, 7.8, 4.1 Hz, 1H), 2.29 (d, J=7.9 Hz, 2H), 2.05-0.75 (m, 42H), 0.68 (s, 3H). $^{13}$C NMR (101 MHz, CDCl$_3$) δ 139.84, 122.55, 61.17, 56.73, 56.07, 50.11, 45.84, 42.32, 39.72, 38.17, 37.59, 36.62, 36.16, 33.95, 31.85 (d, J=6.6 Hz), 29.16, 28.25, 27.96, 26.08, 24.29, 23.08, 21.01, 19.84, 19.29, 19.05, 18.80, 11.93 (d, J=13.3 Hz); IR (film) v max 2935, 2867, 2090, 1463, 1377, 1259, 750 cm$^{-1}$; HRMS (EI+) m/z 411.3872 (M-N$_2$, C$_{29}$H$_{49}$N requires 411.3865).

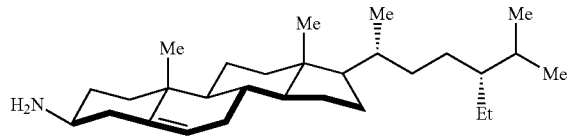

24

3β-Amino-5-sitostene (compound 24)

To a solution of compound 23 (180 mg, 0.44 mmol) in anhydrous diethyl ether (5 mL) at 4° C. was added LiAlH$_4$ powder (25 mg, 0.66 mol) in two equal portions. The reaction was maintained at 4° C. for 30 min, warmed to 22° C., and stirred for 2 h. The reaction was cooled to 4° C. and carefully quenched by slow dropwise addition of ice-cold water. When evolution of H$_2$ gas ceased, the solution was poured into water (10 mL). The organic phase was separated, and the aqueous phase was extracted with ethyl acetate (10 mL×2). The combined organic extracts were washed with saturated NaCl solution (10 mL), dried over anhydrous Na$_2$SO$_4$, and concentrated in vacuo. The resulting solid was dissolved in CHCl$_3$ (10 mL) and residual inorganic salts were removed by filtration. Concentration of the filtrate afforded compound 24 (140 mg, 77%) as a white solid, mp 122-125° C.; $^1$H NMR (400 MHz, CDCl$_3$) δ 5.39-5.27 (m, 1H), 2.75 (q, J=7.2 Hz, 1H), 2.49 (d, J=13.0 Hz, 2H), 2.21-0.74 (m, 42H), 0.67 (s, 3H); $^{13}$C NMR (101 MHz, CDCl$_3$) δ 141.54, 120.89, 56.80, 56.06, 51.90, 50.23, 45.74 (d, J=19.1 Hz), 42.74, 42.32, 39.80, 38.11, 36.56, 36.16, 33.95, 32.14, 31.90, 29.15, 28.26, 26.07, 24.31, 23.07, 21.02, 19.83, 19.45, 19.04, 18.79, 11.93 (d, J=12.1 Hz); IR (film) v max 3360, 3280, 3160, 2926, 2852, 1587, 1462, 1381, 1022, 957, 836, 799, 738 cm$^{-1}$; HRMS (ESI+) m/z 414.4074 (M+H+, $C_{29}H_{51}N$ requires 414.4022).

9H-Fluoren-9-ylmethyl{3-[(3-{(tert-butoxycarbonyl)[3β-sitost-5-en-3-yl]amino}propyl)amino]-3-oxopropyl}carbamate (compound 26)

To a solution of compound 25 (80 mg, 0.11 mmol) in absolute ethanol (3 mL) was added anhydrous hydrazine (17

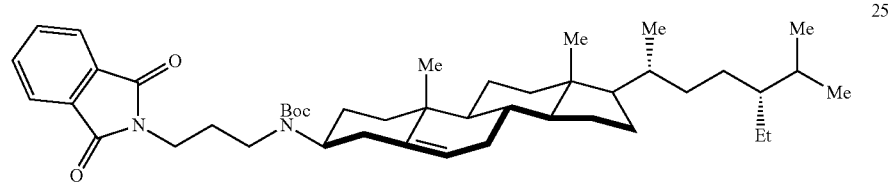

tert-Butyl-3β-sitost-5-en-3-yl[3-(1,3-dioxo-1,3-dihydro-2H-isoindol-2-yl)propyl]carbamate (compound 25)

To DMF (8 mL) was added compound 24 (130 mg, 0.31 mmol), N-(3-bromopropyl)phthalimide (103 mg, 0.38 mmol), and K2CO3 (108 mg, 0.78 mmol). The solution was heated to 60° C. and stirred for 24 h. The reaction was cooled to 22° C., and the solvent removed in vacuo. To the resulting residue was added CH2Cl2 (10 mL). The insoluble material was removed by filtration and washed with CH2Cl2 (2×5 mL). To the combined filtrate and wash solutions containing the crude secondary amine product was added (Boc)2O (135 mg, 0.62 mmol) and DIEA (0.17 mL, 1.24 mmol). The reaction was stirred for 4 h at 22° C. and concentrated in vacuo. Flash column chromatography (hexane, ethyl acetate, 85:15) afforded compound 25 (90 mg, 42% over 2 steps) as a white solid, mp 122-124° C.; 1H NMR (400 MHz, CDCl3) δ 7.88-7.79 (m, 2H), 7.72 (m, 2H), 5.37-5.25 (m, 1H), 3.85 (td, J=6.9, 4.9 Hz, 1H), 3.70 (t, J=7.1 Hz, 2H), 3.15 (br, 2H), 2.06-0.73 (m, 56H), 0.66 (s, 3H); 13C NMR (101 MHz, CDCl3) δ 168.34, 134.07, 133.94, 132.11, 123.35, 123.21, 79.42, 56.71, 56.04, 50.12, 45.83, 42.31, 39.75, 36.17, 35.96, 33.94, 31.88, 29.14, 28.47, 28.26, 26.07, 24.29, 23.06, 20.99, 19.83, 19.41, 19.04, 18.78, 11.93 (d, J=12.2 Hz); IR (film) v max 3340, 2935, 2869, 1713, 1676, 1466, 1365, 1249, 1169, 1143, 907, 730 cm-1; HRMS (ESI+) m/z 723.4980 (M+Na+, C43H65N2O4Na, requires 723.5077).

µL, 0.55 mmol). The solution was heated to 50° C. and stirred for 4 h. The reaction was cooled to 22° C., and a white precipitate was removed by filtration. The filtrate was concentrated in vacuo, and the residue was dissolved in CHCl3 (6 mL). After insoluble material was removed by filtration, concentration of the filtrate in vacuo afforded the phthalimide-deprotected primary amine, a white solid that was carried forward without further purification. To Fmoc-β-Ala-OH (69 mg, 0.22 mmol) in anhydrous CH2Cl2 (2 mL) at 4° C. were added HOBt (30 mg, 0.22 mmol) and EDC (42 mg, 0.22 mmol) followed by stirring at 4° C. for 30 min. To this solution was added dropwise the phthalimide-deprotected primary amine in anhydrous CH2Cl2 (2 mL). The reaction was allowed to warm to 22° C. and stirred for 12 h. The solution was concentrated in vacuo, and flash column chromatography (CH2Cl2, MeOH, 99:1) afforded compound 26 (56 mg, 60% over two steps) as a white solid, mp 86-90° C.; 1H NMR (400 MHz, CDCl3) δ 7.76 (d, J=7.5 Hz, 2H), 7.60 (d, J=7.5 Hz, 2H), 7.39 (t, J=7.4 Hz, 2H), 7.30 (t, J=7.4 Hz, 2H), 6.99 (br, 1H), 5.79 (br, 1H), 5.33 (d, J=4.6 Hz, 1H), 4.35 (d, J=7.2 Hz, 2H), 4.20 (t, J=7.1 Hz, 1H), 3.56-3.46 (m, 2H), 3.25 (m, 4H), 2.44 (m, 2H), 2.07-0.73 (m, 56H), 0.67 (s, 3H); 13C NMR (101 MHz, CDCl3) δ 156.50, 144.04, 141.29, 127.64, 127.03, 125.19, 121.47, 119.94, 66.71, 56.75, 56.06, 50.10, 47.27, 45.84, 42.32, 39.75, 38.45, 36.74, 36.16, 35.98, 33.95, 31.88, 29.15, 28.55, 28.26, 26.08, 24.30, 23.07, 21.01, 19.84, 19.47, 19.04, 18.79, 11.93 (d, J=12.7 Hz); IR (film) v max 3320,

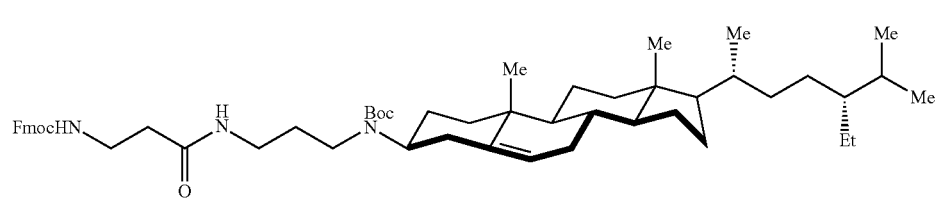

2934, 2869, 1665, 1541, 1450, 1365, 1249, 1167, 1141, 908, 732 cm-1; HRMS (ESI+) m/z 886.5963 (M+Na+, C51H81N3O5Na, requires 668.6074).

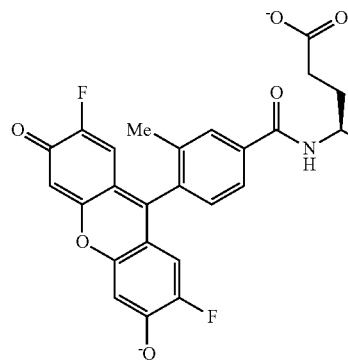

8

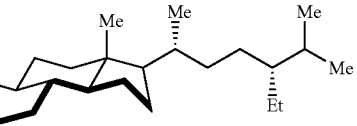

(4S)-5-{[3-({3-[3β-Sitost-5-en-3-ylamino]propyl}amino)-3-oxopropyl]amino}-4-{[4-(2,7-difluoro-6-hydroxy-3-oxo-3H-xanthen-9-yl)-3-methylbenzoyl]amino}-5-oxopentanoic acid (compound 8)

Compound 26 (24.4 mg, 0.028 mmol) was added to DMF (0.5 mL) containing piperidine (20%) and stirred for 30 min at 22° C. The solvent was removed in vacuo to afford the crude primary amine. To a solution of 20 (8.0 mg, 0.014 mmol) in anhydrous DMF (2 mL) at 4° C. was added HOBt (4.0 mg, 0.028 mmol) and EDC (5.4 mg, 0.028 mmol), and the solution was stirred for 30 min. The primary amine derived from 26 in anhydrous DMF (1 mL) was added. The reaction was allowed to warm to 22° C. and stirred for 12 h. The reaction was concentrated in vacuo, TFA/CH2Cl2 (1:1, 2 mL) was added, and the mixture was stirred for 2 h. The solvent was removed in vacuo and the crude product was dissolved in DMSO (2 mL). Purification by preparative reverse-phase HPLC (gradient: 90% H2O, 9.9% MeCN, and 0.1% TFA to 99.9% MeCN and 0.1% TFA over 20 min; retention time=17.5 min (495 nm) afforded compound 8 (11.4 mg, 79%) as an orange solid, mp 192-195° C.; 1H NMR (500 MHz, CD3OD) δ 7.93 (s, 1H), 7.85 (d, J=7.4 Hz, 1H), 7.30 (d, J=7.9 Hz, 1H), 6.86-6.75 (m, 2H), 6.73-6.57 (m, 2H), 5.37 (d, J=4.5 Hz, 1H), 4.44 (dd, J=9.1, 5.1 Hz, 1H), 3.43 (t, J=6.3 Hz, 2H), 2.98 (t, J=7.2 Hz, 2H), 2.89 (d, J=12.1 Hz, 1H), 2.48-0.66 (m, 57H), 0.60 (s, 3H); 13C NMR (126 MHz, CD3OD) δ 176.70, 175.01, 174.05, 169.61, 156.14, 139.52, 138.29-137.87 (m), 136.96, 136.67, 131.10, 130.51, 126.76, 124.79, 112.74 (d, J=22.9 Hz), 106.43, 59.30, 58.05, 57.41, 55.45, 51.45, 49.52, 49.35, 49.18, 49.07, 49.07-48.88 (m), 48.84, 48.58 (d, J=21.4 Hz), 47.26, 43.40 (d, J=8.9 Hz), 40.99, 38.24, 37.81, 37.41, 37.19-36.60 (m), 36.34, 35.07, 32.98 (d, J=13.5 Hz), 31.52, 30.37, 29.32, 27.97 (d, J=9.4 Hz), 27.15, 26.33, 25.24, 24.14, 22.05, 20.21, 19.69, 19.62-19.17 (m), 12.32 (d, J=9.0 Hz); IR (film) ν max 3306, 2956, 2869, 1671, 1541, 1302, 1201, 1135, 841, 801, 724 cm-1; HRMS (ESI−) m/z 1033.5874 (M−H+, C61H80F2N4O8 requires 1033.5871).

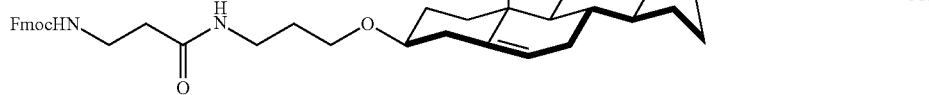

28

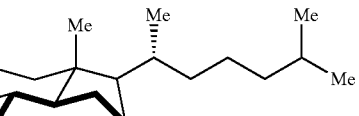

9H-fluoren-9-ylmethyl{3-[(3-{[3β-cholest-5-en-3-yl]oxy}propyl)amino]-3-oxopropyl}carbamate (compound 28)

To Fmoc-β-Ala-OH (380 mg, 1.22 mmol) in anhydrous CH2Cl2 (5 mL) at 4° C. was added HOBt (165 mg, 1.22 mmol) and EDC (234 mg, 1.22 mmol), and the mixture was stirred at 4° C. for 30 min. To this solution was added compound 27, synthesized as previously reported, (350 mg, 0.81 mmol) in anhydrous CH2Cl2 (5 mL). The reaction was allowed to warm to 22° C. and was stirred for 12 h. The solution was diluted with CH2Cl2 (10 mL) and washed with saturated aqueous NaHCO3 (10 mL) and saturated aqueous NaCl (10 mL). The organic layer was dried over anhydrous Na2SO4 and concentrated in vacuo. Flash column chromatography (CH2Cl2/MeOH, 99:1) afforded compound 28 (515 mg, 87%) as a glassy solid, mp 148-150° C.; 1H NMR (400 MHz, CDCl3) δ 7.76 (d, J=7.5 Hz, 2H), 7.59 (d, J=7.5 Hz, 2H), 7.39 (t, J=7.4 Hz, 2H), 7.30 (t, J=7.4 Hz, 2H), 6.34 (br, 1H), 5.58 (br, 1H), 5.34-5.26 (m, 1H), 4.35 (d, J=7.2 Hz, 2H), 4.20 (t, J=7.1 Hz, 1H), 3.61-3.44 (m, 4H), 3.38 (dt, J=11.4, 5.8 Hz, 2H), 3.16-3.04 (m, 1H), 2.46-0.79 (m, 44H), 0.69-0.63 (m, 3H); 13C NMR (101 MHz, CDCl3) δ 171.19, 156.62, 144.12, 141.42, 140.64, 127.79, 127.17, 125.29, 122.02, 120.09, 79.46, 67.37, 66.90, 56.87, 56.29, 50.27, 47.35, 42.44, 39.89, 39.65, 39.23, 38.86, 37.24, 36.96, 36.33, 35.99 (d, J=15.0 Hz), 32.00 (d, J=5.9 Hz), 29.24, 28.61, 28.36, 28.15, 24.40, 23.96, 22.96, 22.70, 21.17, 19.49, 18.86, 11.99; IR (film) ν max 3306, 2934, 2867, 1682, 1639, 1537, 1448, 1376, 1342, 1268, 1240, 1103, 1018, 908, 735 cm-1; HRMS (ESI+) m/z 775.4972 (M+K+, C48H68N2O4K requires 775.4816).

over 20 min; retention time=16.5 min (495 nm) afforded compound 9 (13.1 mg, 87%) as an orange solid, mp 192-194° C.; 1H NMR (400 MHz, CD3OD) δ 8.01 (s, 1H), 7.94 (d, J=7.9 Hz, 1H), 7.28-7.36 (m, 1H), 7.04-6.85 (m, 2H), 6.82-6.70 (m, 2H), 5.32-5.26 (m, 1H), 4.60-4.54 (m, 1H), 3.56-3.45 (m, 4H), 3.45-3.36 (m, 2H), 3.28-3.22 (m, 4H), 3.17-3.04 (m, 2H), 2.62-0.81 (m, 46H), 0.67 (s, 3H); 13C NMR (101 MHz, CD3OD) δ 190.52, 183.25, 180.16, 173.46, 171.19, 161.26, 155.36, 150.34, 141.55, 136.58, 133.73, 130.91, 126.48, 122.52, 106.27, 80.31, 67.05, 66.56, 57.81,

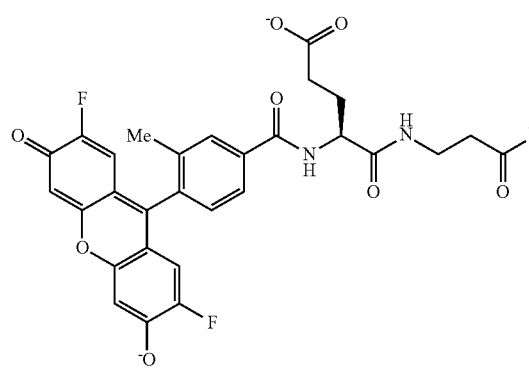

9

(4S)-5-{[3-({3-[3β-Cholest-5-en-3-yloxy]propyl}amino)-3-oxopropyl]amino}-4-{[4-(2,7-difluoro-6-hydroxy-3-oxo-3H-xanthen-9-yl)-3-methylbenzoyl]amino}-5-oxopentanoic acid (compound 9)

Compound 28 (15.0 mg, 0.020 mmol) was added to DMF (0.5 mL) containing piperidine (20%) and stirred for 30 min at 22° C. The solvent was removed in vacuo to afford the crude primary amine. To a solution of compound 20 (11.3 mg, 57.19, 51.31, 43.21, 40.79, 40.41, 39.93, 38.54, 38.11, 37.76 (d, J=16.8 Hz), 37.08, 36.94, 36.78, 36.34, 32.82 (d, J=11.2 Hz), 31.33, 30.49, 29.14 (d, J=15.5 Hz), 28.87, 27.88, 25.06, 24.68, 23.15, 22.89, 21.91, 19.81 (d, J=5.1 Hz), 19.17, 12.28. IR (film) ν max 3369, 2925, 2853, 2076, 1646, 1543, 1464, 1375, 1314, 1193, 1117, 971, 735 cm-1; HRMS (ESI-) m/z 1006.5441 (M−H+, C59H74F2N3O9 requires 1006.5399).

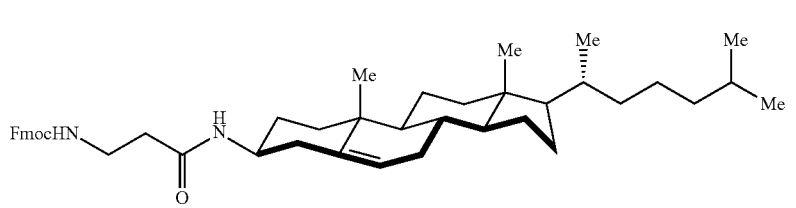

31

0.020 mmol) in anhydrous DMF (2 mL) at 4° C. was added HOBt (5.5 mg, 0.040 mmol) and EDC (8.0 mg, 0.040 mmol) and the solution was stirred for 30 min. The primary amine derived from compound 28 in anhydrous DMF (1 mL) was added. The reaction was allowed to warm to 22° C. and was stirred for 12 h. The reaction was concentrated in vacuo, TFA/CH2Cl2 (1:1, 2 mL) was added, and the solution stirred at 22° C. for 2 h. The solvent was removed in vacuo and the crude product was dissolved in DMSO (2 mL). Purification by preparative reverse-phase HPLC (gradient: 90% H2O, 9.9% MeCN, and 0.1% TFA to 99.9% MeCN and 0.1% TFA (9H-fluoren-9-yl)methyl(3-{[3β-cholest-5-en-3-yl]amino}-3-oxopropyl)carbamate (compound 31)

Fmoc-β-Ala-Cl (compound 29, 170 mg, 0.54 mmol, prepared by treatment of Fmoc-β-Ala-OH with excess SOCl2 for 1 h followed by removal of SOCl2 in vacuo) was dissolved in anhydrous CH2Cl2 (5 mL). A solution of 3β-amino-5-cholestene (compound 30, 250 mg, 0.65 mmol) and 4-dimethylaminopyridine (DMAP, 15 mg, 0.10 mmol) in anhydrous CH2Cl2 was slowly added and the solution was stirred at 22° C. for 30 min. The reaction was diluted with CH2Cl2 (25 mL) and filtered to remove precipitated solids. The resulting filtrate was concentrated in vacuo and purified via flash column chromatography (CH2Cl2, MeOH, 99:1) to afford compound 31 (128 mg, 35%) as a white solid, mp 124-128° C.; 1H NMR (400 MHz, CDCl3) δ 7.75 (d, J=7.5 Hz, 2H), 7.58 (d, J=7.5 Hz, 2H), 7.39 (t, J=7.4 Hz, 2H), 7.30 (t, J=7.3 Hz, 2H), 5.54 (br, 1H), 5.41-5.32 (m, 2H), 4.36 (m, 2H), 4.20 (t, J=6.9 Hz, 1H), 3.69 (m, 1H), 3.48 (m, 2H), 2.39 (m, 2H), 2.29 (dd, J=13.2, 2.6 Hz, 1H), 2.14-0.82 (m, 39H), 0.69 (s, 3H); 13C NMR (101 MHz, CDCl3) δ 170.28, 156.57, 144.00, 141.33, 140.12, 127.65, 127.04, 125.07, 122.07, 119.93, 77.32, 77.00, 76.68, 66.78, 56.74, 56.23, 50.16, 49.86, 47.30, 42.34, 39.78, 39.54, 39.31, 37.86, 37.22, 36.57, 36.22, 35.79, 31.87 (d, J=4.6 Hz), 29.18, 28.20, 27.99, 24.27, 23.86, 22.77, 22.53, 20.99, 19.31, 18.73, 11.86; IR (film) ν max 3313, 2933, 2867, 1686, 1636, 1534, 1449, 1267, 1148, 1023, 992, 735 cm-1; HRMS (ESI+) m/z 701.4615 (M+Na+, C45H62N2O3Na, requires 701.4658).

vacuo, and flash column chromatography (CH2Cl2/MeOH, 98/2) afforded compound 32 (23.8 mg, 71%) as a white solid, mp 178-180° C.; 1H NMR (400 MHz, CDCl3) δ 7.76 (d, J=7.5 Hz, 2H), 7.59 (d, J=7.4 Hz, 2H), 7.39 (t, J=7.4 Hz, 2H), 7.30 (t, J=7.4 Hz, 2H), 6.52 (br, 1H), 5.66-5.49 (m, 2H), 5.31 (d, J=11.0 Hz, 1H), 4.35 (d, J=7.0 Hz, 2H), 4.20 (t, J=7.1 Hz, 1H), 3.65 (m, 1H), 3.58-3.42 (m, 4H), 2.39 (m, 4H), 2.24 (m, 1H), 2.12-0.78 (m, 39H), 0.66 (s, 3H); 13C NMR (101 MHz, CDCl3) δ 170.64, 156.46, 143.99, 141.30, 139.96, 127.68, 127.05, 125.17, 122.18, 119.97, 66.76, 56.67, 56.13, 49.97 (d, J=13.5 Hz), 47.25, 42.29, 39.62 (d, J=19.0 Hz), 39.21, 37.77, 36.51, 36.19, 35.98, 35.80, 35.54 (d, J=12.7 Hz), 31.80, 29.08, 28.13 (d, J=20.8 Hz), 28.01-27.92 (m), 24.27, 23.84, 22.83, 22.57, 20.94, 19.30, 18.72, 11.86; IR (film) ν max 3310, 2932, 2867, 1687, 1637, 1536, 1450, 1367, 1273, 1148, 1105, 1025, 739 cm-1; HRMS (ESI+) m/z 772.4980 (M+Na+, C48H67N3O4Na, requires 772.5029).

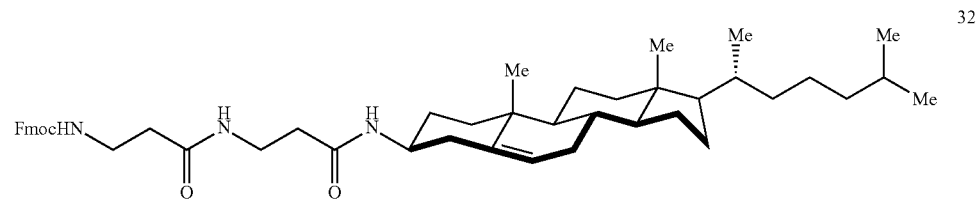

(9H-fluoren-9-yl)methyl(3-((3-{[3β-cholest-5-en-3-yl]amino}-3-oxopropyl)amino)-3-oxopropyl)carbamate (compound 32)

Compound 31 (30.0 mg, 0.045 mmol) was added to DMF (0.5 mL) containing piperidine (20%) and stirred for 30 min at 22° C. The solvent was removed in vacuo to afford the crude primary amine. To a solution of Fmoc-β-Ala-OH (27.5 mg, 0.090 mmol) in anhydrous DMF (2 mL) at 4° C. were added HOBt (12.0 mg, 0.090 mmol) and EDC (17.0 mg, 0.090 mmol) and the solution was stirred for 30 min. The primary amine derived from compound 31 in anhydrous DMF (1 mL) was added. The reaction was allowed to warm to 22° C. and stirred for 12 h. The reaction was concentrated in

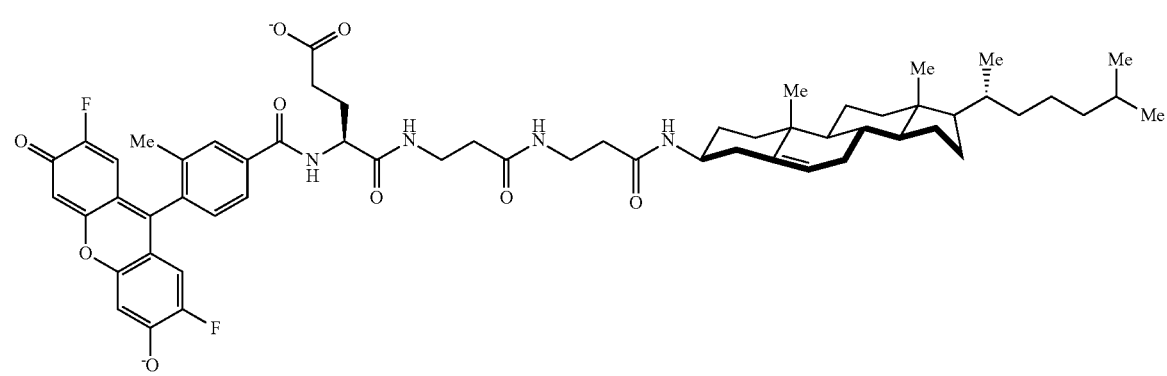

(4S)-4-(4-(2,7-difluoro-6-hydroxy-3-oxo-3H-xanthen-9-yl)-3-methylbenzamido)-5-((3-{(3-{[3β-cholest-5-en-3-yl]amino}-3-oxopropyl)amino)-3-oxopropyl)amino)-5-oxopentanoic acid (compound 10)

Compound 32 (21.0 mg, 0.028 mmol) was added to DMF (0.5 mL) containing piperidine (20%) and stirred for 30 min at 22° C. The solvent was removed in vacuo to afford the crude primary amine. To a solution of compound 20 (8.0 mg, 0.014 mmol) in anhydrous DMF (2 mL) at 4° C. was added HOBt (4.0 mg, 0.028 mmol) and EDC (5.4 mg, 0.028 mmol) and the solution was stirred for 30 min. The primary amine derived from compound 32 in anhydrous DMF (1 mL) was added. The reaction was allowed to warm to 22° C. and stirred for 12 h. The reaction was concentrated in vacuo. TFA/CH2Cl2 (1:1, 2 mL) was added and the solution was stirred for 2 h at 22° C. The solvent was removed in vacuo, and the crude product was dissolved in DMSO (2 mL). Purification by preparative reverse-phase HPLC (gradient: 90% H2O, 9.9% MeCN, and 0.1% TFA to 99.9% MeCN and 0.1% TFA over 20 min; retention time=19.0 min (495 nm) afforded compound 10 (10.2 mg, 71%) as a orange solid, mp 192-194° C.; 1H NMR (500 MHz, CD3OD) δ 8.01 (s, 1H), 7.96 (d, J=6.8 Hz, 1H), 7.33 (d, J=7.7 Hz, 1H), 6.85 (m, 2H), 6.66 (m, 2H), 5.32 (m, 1H), 3.64-3.52 (m, 2H), 3.52-3.44 (m, 2H), 2.58-0.81 (m, 53H), 0.69 (s, 3H); 13C NMR (126 MHz, CD3OD) δ 175.61, 173.36, 168.58, 163.08, 155.99, 141.21, 137.35, 136.58, 135.94, 130.61, 130.43, 129.83, 126.05, 122.33, 113.29, 111.80, 106.20, 57.46, 56.87, 50.95, 50.55, 43.30, 42.94, 40.46, 40.17, 39.35, 38.62, 37.24, 36.83, 36.51, 32.51 (d, J=10.1 Hz), 29.19, 28.85, 28.63, 24.84, 24.45, 23.09, 22.83, 21.59, 19.83, 19.64, 19.07, 12.21; IR (film) ν max 3305, 2932, 2871, 1646, 1541, 1371, 1306, 1188, 952, 750 cm-1; HRMS (ESI-) m/z 1019.5361 (M-H+, C59H74F2N4O9 requires 1019.5351).

Hz, 2H), 4.21 (t, J=7.0 Hz, 1H), 3.50-3.45 (m, 2H), 2.54 (t, J=5.7 Hz, 2H), 2.33 (d, J=7.8 Hz, 2H), 2.07-0.80 (m, 38H), 0.69 (s, 3H); 13C NMR (101 MHz, CDCl3) δ 171.86, 156.32, 143.95, 141.32, 139.48, 127.70, 127.05, 125.09, 122.87, 119.99, 74.52, 66.76, 56.70, 56.15, 50.03, 47.25, 42.33, 39.64 (d, J=19.9 Hz), 38.14, 36.97, 36.60, 36.20, 35.81, 34.72, 31.89 (d, J=6.0 Hz), 28.25, 28.04, 27.82, 24.30, 23.85, 22.85, 22.59, 21.05, 19.33, 18.74, 11.88; IR (film) ν max 3356, 2946, 2868, 1721, 1512, 1450, 1376, 1263, 1189, 1006, 735 cm-1; HRMS (ESI+) m/z 702.4473 (M+Na+, C45H61NO4Na, requires 702.4498).

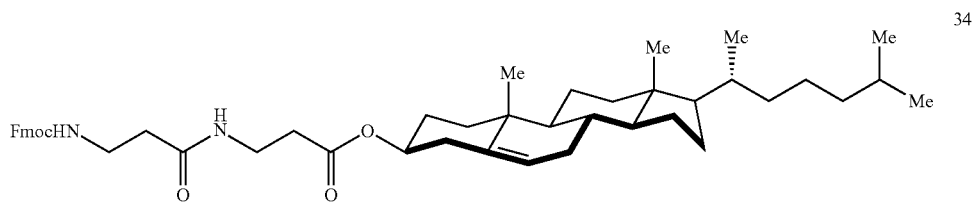

(34)

Cholesteryl 3-(3-((((9H-fluoren-9-yl)methoxy)carbonyl)amino)propanamido) propanoate (compound 34)

Compound 33 (200 mg, 0.30 mmol) was added to DMF (1.0 mL) containing piperidine (20%) and stirred for 30 min at 22° C. The solvent was removed in vacuo to afford the crude primary amine. To a solution of Fmoc-β-Ala-OH (102 mg, 0.33 mmol) in anhydrous DMF (3 mL) at 4° C. were added HOBt (45 mg, 0.33 mmol) and EDC (64 mg, 0.33 mmol) and the solution was stirred for 30 min. The primary amine derived from 33 in anhydrous DMF (3 mL) was added. The reaction was allowed to warm to 22° C. and stirred for 12 h. The reaction was concentrated in vacuo, and flash column chromatography (CH2Cl2/MeOH, 98/2) afforded compound 34 (150 mg, 52%) as a white foam, mp 158-160° C.; 1H NMR

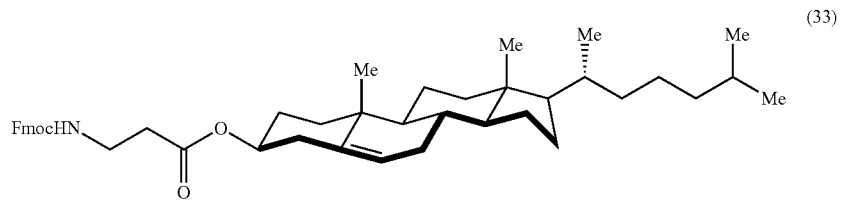

(33)

Cholesteryl 3-((((9H-fluoren-9-yl)methoxy)carbonyl)amino)propanoate (compound 33)

A solution of cholesterol (1, 681 mg, 1.76 mmol) and 4-dimethylaminopyridine (60 mg, 0.50 mmol) in anhydrous CH2Cl2 (5 mL) was slowly added to Fmoc-β-Ala-Cl (compound 29, 500 mg, 1.60 mmol) in anhydrous CH2Cl2 (5 mL) and the solution was stirred at 22° C. for 12 h. The reaction was diluted with CH2Cl2 (25 mL) and filtered to remove precipitated solids. The resulting filtrate was concentrated in vacuo and purified via flash column chromatography (hexane, ethyl acetate, 7:3) to provide compound 33 (590 mg, 55%) as a white foam, mp 102-104° C.; 1H NMR (400 MHz, CDCl3) δ 7.76 (d, J=7.5 Hz, 2H), 7.59 (d, J=6.9 Hz, 2H), 7.40 (t, J=7.4 Hz, 2H), 7.31 (t, J=7.4 Hz, 2H), 5.39 (d, J=3.8 Hz, 1H), 5.39-5.33 (m, 1H), 4.66 (d, J=8.4 Hz, 1H), 4.38 (d, J=7.1 (400 MHz, CDCl3) δ 7.75 (d, J=7.3 Hz, 2H), 7.59 (d, J=7.3 Hz, 2H), 7.39 (t, J=7.2 Hz, 2H), 7.30 (t, J=7.1 Hz, 2H), 6.24 (br, 1H), 5.60 (br, 1H), 5.35 (m, 1H), 4.62 (m, 1H), 4.35 (d, J=6.5 Hz, 2H), 4.20 (t, J=6.6 Hz, 1H), 3.61-3.45 (m, 4H), 2.50 (t, J=6.1 Hz, 2H), 2.45-2.35 (m, 1H), 2.29 (d, J=7.3 Hz, 2H), 2.04-0.78 (m, 39H), 0.67 (s, 3H); 13C NMR (101 MHz, CDCl3) δ 172.09, 171.42, 156.61, 144.07, 141.39, 139.49, 127.77, 127.15, 125.25, 122.98, 120.05, 74.71, 66.83, 56.76, 56.23, 50.07, 47.34, 42.39, 39.71 (d, J=18.3 Hz), 38.19, 37.19, 37.00, 36.64, 36.29, 35.97 (d, J=15.7 Hz), 35.03, 34.37, 31.93 (d, J=5.7 Hz), 28.33, 28.12, 27.87, 24.37, 23.94, 22.94, 22.68, 21.11, 19.38, 18.82, 11.95; IR (film) ν max 3314, 2937, 1729, 1687, 1640, 1544, 1449, 1377, 1269, 1186, 1027, 739 cm-1; HRMS (ESI+) m/z 773.4793 (M+Na+, C48H67N3O4Na, requires 773.4869).

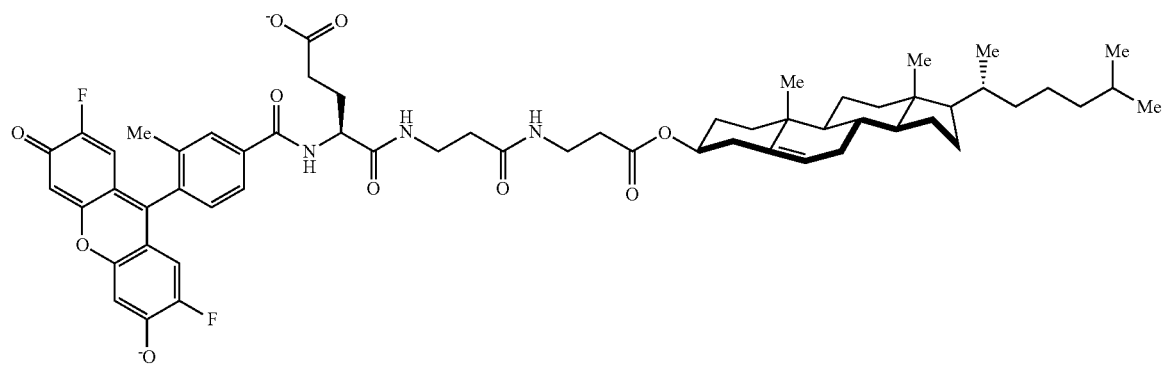

(4S)-4-(4-(2,7-difluoro-6-hydroxy-3-oxo-3H-xanthen-9-yl)-3-methylbenzamido)-5-((3-((3-{[3-cholester-3-yl]oxy}3-oxopropyl)amino)-3-oxopropyl)amino)-5-oxopentanoic acid (compound 11)

Compound 34 (21.0 mg, 0.028 mmol) was added to DMF (0.5 mL) containing piperidine (20%) and stirred for 30 min at 22° C. The solvent was removed in vacuo to afford the crude primary amine. To a solution of compound 20 (8.0 mg, 0.014 mmol) in anhydrous DMF (2 mL) at 4° C. were added HOBt (4.0 mg, 0.028 mmol) and EDC (5.4 mg, 0.028 mmol) and the solution was stirred for 30 min. The primary amine derived from compound 34 in anhydrous DMF (1 mL) was added. The reaction was allowed to warm to 22° C. and stirred for 12 h. The reaction was concentrated in vacuo. TFA/CH2Cl2 (1:1, 2 mL) was added and the solution stirred at 22° C. for 2 h. The solvent was removed in vacuo and the crude product was dissolved in DMSO (2 mL). Purification by preparative reverse-phase HPLC (gradient: 90% H2O, 9.9% MeCN, and 0.1% TFA to 99.9% MeCN and 0.1% TFA over 20 min; retention time=17.0 min (495 nm) afforded compound 11 (10.5 mg, 73%) as an orange solid, mp 180-184° C.; 1H NMR (500 MHz, CD3OD) δ 8.03 (s, 1H), 7.97 (d, J=7.7 Hz, 1H), 7.36 (d, J=7.9 Hz, 1H), 6.84 (m, 2H), 6.76 (m, 2H), 5.32 (d, J=4.2 Hz, 1H), 4.59 (m, 2H), 3.59-3.39 (m, 4H), 2.58-2.48 (m, 4H), 2.43 (dd, J=10.6, 6.4 Hz, 2H), 2.29 (d, J=7.7 Hz, 2H), 2.16 (s, 3H), 2.06-0.78 (m, 40H), 0.69 (s, 3H); 13C NMR (126 MHz, CD3OD) δ 174.83, 171.84, 171.03, 167.27, 148.36, 141.22, 139.66, 138.91 (d, J=9.8 Hz), 135.96, 134.86, 134.59, 131.93, 129.58-129.33 (m), 129.20 (d, J=21.2 Hz), 128.73, 128.43, 126.53, 125.57 (d, J=2.6 Hz), 124.73 (d, J=14.4 Hz), 123.97, 122.66, 121.83, 119.23, 118.47, 113.50, 112.21, 104.60, 73.79, 56.06, 55.49, 53.34, 49.49, 46.96, 43.56, 41.51, 39.05, 38.74, 37.21, 36.23, 35.77, 35.40, 35.11, 34.63 (d, J=15.8 Hz), 33.33, 31.09 (d, J=12.1 Hz), 29.65, 29.06, 27.39, 27.20, 26.85, 26.11, 23.37, 23.00, 21.47, 21.21, 20.19, 18.07 (d, J=16.6 Hz), 17.48, 10.58; IR (film) ν max 3298, 2930, 2868, 1725, 1643, 1610, 1534, 1456, 1374, 1295, 1188, 1024, 952, 838, 732 cm-1; HRMS (ESI−) m/z 1020.5208 (M−H+, C59H73F2N3O10 requires 1020.5191).

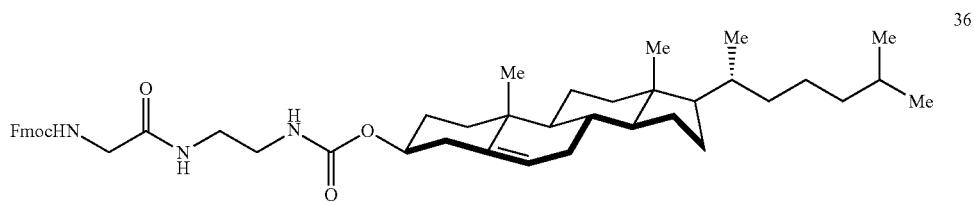

9H-fluoren-9-ylmethyl (3-((3-(((({[cholester-3-yl]oxy}carbonyl)amino)ethyl)amino)-2-oxoethyl)amino)carbamate (compound 36)

A solution of cholesteryl chloroformate (compound 35, 500 mg, 1.11 mmol) in CH2Cl2 (5 mL) was very slowly added to a solution of ethylene diamine (1.50 mL, 22.26 mmol) in CH2Cl2 (10 mL). The reaction was allowed to stir at 22° C. for 2 h. The excess diamine was removed in vacuo, the resulting solid was dissolved in CH2Cl2 (10 mL), and the organic layer was washed with aqueous NaOH (1 M, 10 mL). The organic phase was dried over anhydrous Na2SO4, and concentrated in vacuo to provide the primary amine produc, which was used without further purification. To a solution of Fmoc-Gly-OH (104 mg, 0.35 mmol) in anhydrous CH2Cl2 (5 mL) at 4° C. was added HOBt (47 mg, 0.35 mmol) and EDC (67 mg, 0.35 mmol) and the solution was stirred for 30 min. The primary amine derived from compound 35 (150 mg, 0.32 mmol) in anhydrous CH2Cl2 (3 mL) was added. The reaction was allowed to warm to 22° C. and stirred for 12 h. The reaction was concentrated in vacuo, and purified by flash column chromatography (CH2Cl2/MeOH, 98/2) to afford compound 36 (130 mg, 56%) as a white foam, mp 82-84° C.; 1H NMR (400 MHz, CDCl3) δ 7.76 (d, J=7.5 Hz, 2H), 7.60 (d, J=7.2 Hz, 2H), 7.40 (t, J=7.3 Hz, 2H), 7.31 (td, J=7.5, 1.1 Hz, 2H), 6.74 (br, 1H), 5.46 (br, 1H), 5.31 (m, 1H), 5.04 (br, 1H), 4.43 (d, J=7.2 Hz, 2H), 4.22 (t, J=6.9 Hz, 1H), 3.87 (m, 1H), 3.39 (m, 2H), 3.32 (m, 2H), 2.92 (d, J=32.0 Hz, 2H), 2.38-0.73 (m, 40H), 0.65 (s, 3H); 13C NMR (101 MHz, CDCl3) δ 170.08, 162.84, 156.80, 143.88, 141.40, 139.71, 127.87, 127.22, 125.23, 122.75, 120.12, 74.93, 67.38, 56.72, 56.27, 49.99, 47.24, 44.59, 42.39, 39.72 (d, J=18.3 Hz), 38.59, 36.98, 36.66 (d, J=19.2 Hz), 36.31, 35.91, 31.78 (d, J=19.0 Hz), 28.53-28.02 (m), 24.35, 23.97, 22.94, 22.68, 21.11, 19.39, 18.83, 11.95; IR (film) v max 3319, 2937, 2867, 1665, 1527, 1450, 1382, 1252, 1153, 1031, 1009, 737 cm-1; HRMS (ESI−) m/z 786.4638 (M+Cl−, C59H73F2N3O10Cl requires 786.4613).

22.20, 20.09 (d, J=17.0 Hz), 19.48, 12.59; IR (film) v max 3312, 2931, 2867, 1644, 1610, 1526, 1463, 1373, 1266, 1188, 1161, 1026, 952, 874, 733 cm-1; HRMS (ESI−) m/z 1021.5169 (M−H+, C59H73F2N3O10 requires 1021.5144).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

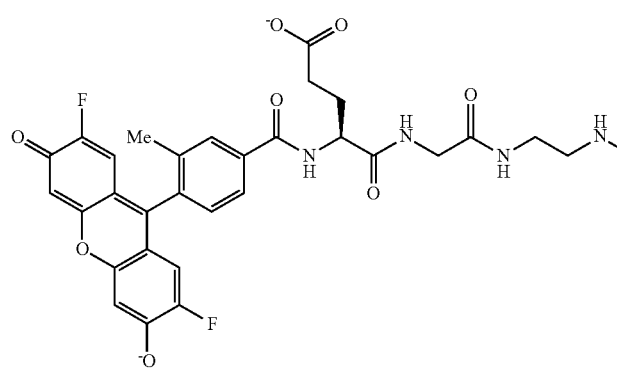

12

(4S)-4-(4-(2,7-difluoro-6-hydroxy-3-oxo-3H-xanthen-9-yl)-3-methylbenzamido)-5-(3-((3-((({[3-cholester-3-yl]oxy}carbonyl)amino)ethyl)amino)-2-oxoethyl)amino)-5-oxopentanoic acid (compound 12)

Compound 36 (21.0 mg, 0.028 mmol) was added to DMF (0.5 mL) containing piperidine (20%) and stirred for 30 min at 22° C. The solvent was removed in vacuo to afford the crude primary amine. To a solution of 20 (8.0 mg, 0.014 mmol) in anhydrous DMF (2 mL) at 4° C. was added HOBt (4.0 mg, 0.028 mmol) and EDC (5.4 mg, 0.028 mmol) and the solution was stirred for 30 min. The primary amine derived from 36 in anhydrous DMF (1 mL) was added. The reaction was allowed to warm to 22° C. and stirred for 12 h. The reaction was concentrated in vacuo. TFA/CH2Cl2 (1:1, 2 mL) was added and the solution was stirred at 22° C. for 2 h. The solvent was removed in vacuo and the crude product was dissolved in DMSO (2 mL). Purification by preparative reverse-phase HPLC (gradient: 90% H2O, 9.9% MeCN, and 0.1% TFA to 99.9% MeCN and 0.1% TFA over 20 min; retention time=17.0 min (495 nm) afforded compound 12 (9.0 mg, 63%) as an orange solid, mp 186-190° C.; 1H NMR (500 MHz, CD3OD) δ 8.06 (s, 1H), 8.01 (d, J=7.0 Hz, 1H), 7.35 (d, J=7.8 Hz, 1H), 7.05-6.90 (m, 2H), 6.90-6.69 (m, 2H), 5.30-5.24 (m, 1H), 4.57-4.48 (m, 1H), 4.42-4.32 (m, 2H), 4.18 (s, 1H), 3.91 (dd, J=116.3, 16.9 Hz, 2H), 3.41-3.33 (m, 2H), 3.31-3.25 (m, 2H), 2.62-2.51 (m, 2H), 2.40-0.78 (m, 43H), 0.68 (s, 3H); 13C NMR (126 MHz, CD3OD) δ 176.93, 174.60, 171.87, 169.77, 158.73, 150.37, 141.11, 130.75, 128.54, 127.59, 125.98, 124.67, 123.60, 121.25, 120.48, 114.22, 106.58, 75.79, 58.06, 57.50, 51.48, 43.90, 43.52, 41.54-41.39 (m), 41.54-41.34 (m), 40.98 (dd, J=42.1, 18.4 Hz), 39.75, 38.26, 37.75, 37.42, 37.13, 33.10 (d, J=15.4 Hz), 31.59, 29.56-29.12 (m), 27.36, 25.38, 25.01, 23.47, 23.22,

The invention claimed is:

1. A compound comprising: a structure of Formula 1, Formula 2, Formula 3, or Formula 4 or derivative, salt, or prodrug thereof:

Formula 1

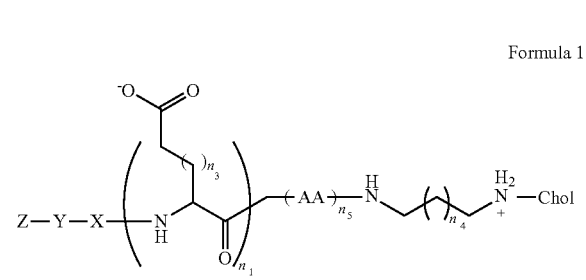

Formula 2

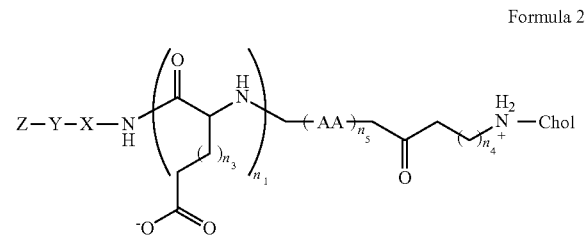

Formula 3

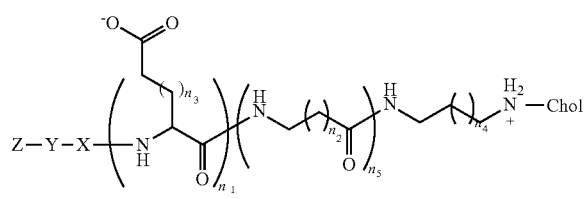

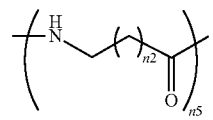

includes at least one beta alanine in Formula 3; and

Formula 4

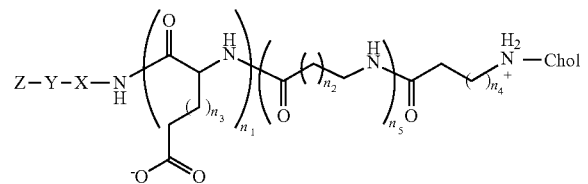

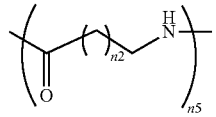

wherein:

$n_1$ is 1-6;

$n_2$ is 0-6;

$n_3$ is 0-6;

$n_4$ is 0-6;

n5 is 1-10;

AA is one or more natural or non-natural amino acids, essential amino acids, or non-essential amino acids, or derivatives of amino acids having L or D configuration, wherein AA includes at least one beta alanine;

Chol is a cholesterol derivative;

X is nothing or a coupling group;

Y is nothing or a linker;

Z is an agent for delivery into a cell;

includes at least one beta alanine in Formula 4.

2. The compound of claim 1, wherein the compound has a structure of Formula 5 or Formula 6 or derivative, salt, or prodrug thereof, R is hydrogen, methyl, ethyl, or alkyl, which is substituted or unsubstituted, straight or branched, saturated or unsaturated Formula 5

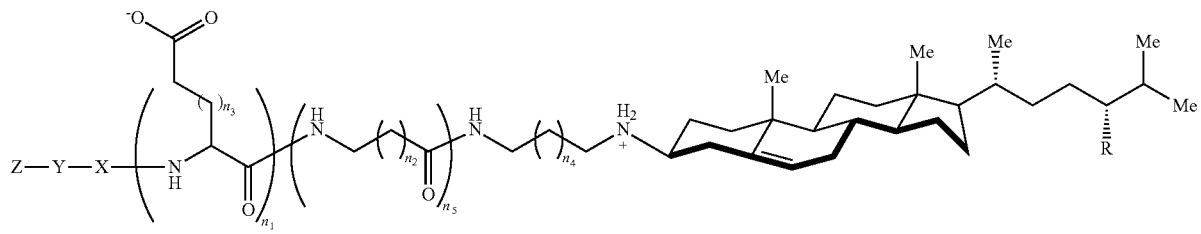

Formula 6

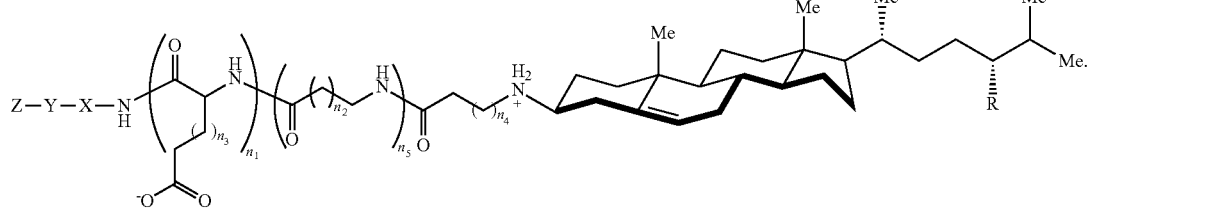

wherein:

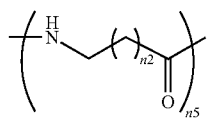

includes at least one beta alanine in Formula 5; and

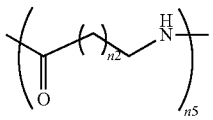

includes at least one beta alanine in Formula 6.

3. The compound of claim 1, wherein the cholesterol derivative is selected from the group consisting of cholesterol, dihydrocholesterol, sitosterol, cholesteryl, dihydrocholesteryl, or derivative thereof.

4. The compound of claim 3, wherein the cholesterol derivative is a cholesteryl or dihydrocholesteryl or sitosterol so that the compound includes a cholesterylamine or a dihydrocholesterylamine or a sitosterylamine.

5. The compound of claim 1, wherein the linker Y is selected from a straight chain or branched or cyclic substituted or unsubstituted alkyl group having C1-C100, a polypeptide, a polynucleotide, polysaccharide, a polyethylene glycol, a biodegradable linker, or combinations thereof.

6. The compound of claim 1, wherein the coupling group X includes an amide, ether, ester, carbamate, alkyl, aryl, alkene, triazole, amine, or alkanol or is derived from a coupling reaction between the linker and a coupling agent selected from a dithio diacid, a dicarboxylic acid, an acrylic moiety, a diazide, a styrene, a vinyl carboxylic acid, a urethane, a vinyl acetate, a vinyl ether, a Diels-Alder reagent, disulfides, disulfides, hydrazones, imines, acetals, orthoesters, or other acid-labile or redox sensitive groups that allow release of agents in cells or tissues, photopolymerizable moiety, derivatives thereof, and combinations thereof.

7. The compound of claim 1, wherein the agent is selected from therapeutic agents, imaging agents, diagnostic agents, toxic agents, or combinations thereof.

8. The compound of claim 7, wherein the agent is selected from a protein, peptide, polypeptide, nucleic acid, RNA, DNA, RNA/DNA hybrid, PNA, morpholinos, oligomers, siRNA, carbohydrates, lipids, markers, luminophores, tracer substances, molecular probes, oligopeptides, drugs, prodrug, a small molecule, or combinations thereof.

9. The compound of claim 1, wherein the compound includes one or more beta-alanine residues between the X and the Chol.

10. The compound of claim 1, wherein the compound includes wherein the compound has a structure of Formula 7 or derivative, salt, or prodrug thereof;

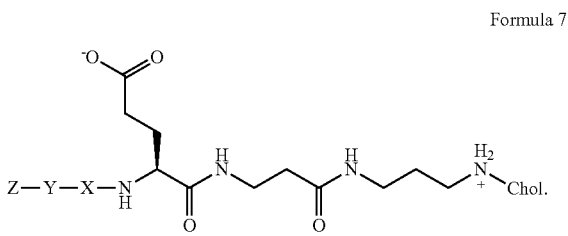

Formula 7

11. A pharmaceutical composition comprising:
the compound of claim 1; and
a pharmaceutically acceptable carrier having the compound.

12. A method of delivering an agent into a cell, the method comprising:
providing the compound of claim 1 having the agent; and
administering the compound to the cell.

13. The method of claim 12, wherein the administering is in vivo.

14. The method of claim 12, wherein the administering is in vitro.

15. The method of claim 12, wherein the cell is in a subject in need of the agent.

16. The method of claim 15, wherein the agent is a therapeutic agent for treating a disease or symptom of the disease.

17. The method of claim 16, wherein the therapeutic agent is administered in a therapeutically effective amount to treat the disease or symptom of the disease.

18. A system for delivering an agent into a cell, the system comprising: the compound of claim 1; and a release compound configured for releasing the compound into cytoplasm of the cell.

19. The system of claim 18, wherein the release compound includes an endosomal disrupting agent.

* * * * *